(12) United States Patent
Saadat et al.

(10) Patent No.: US 8,078,266 B2
(45) Date of Patent: *Dec. 13, 2011

(54) FLOW REDUCTION HOOD SYSTEMS

(75) Inventors: Vahid Saadat, Atherton, CA (US); Edmund Tam, Mountain View, CA (US); Chris A. Rothe, San Mateo, CA (US); David Miller, Cupertino, CA (US); Ruey-Feng Peh, Singapore (SG)

(73) Assignee: Voyage Medical, Inc., Redwood City, CA (US)

( * ) Notice: Subject to any disclaimer, the term of this patent is extended or adjusted under 35 U.S.C. 154(b) by 710 days.

This patent is subject to a terminal disclaimer.

(21) Appl. No.: 12/026,455

(22) Filed: Feb. 5, 2008

(65) Prior Publication Data

US 2008/0188759 A1 Aug. 7, 2008

Related U.S. Application Data

(63) Continuation-in-part of application No. 11/259,498, filed on Oct. 25, 2005, now Pat. No. 7,860,555.

(60) Provisional application No. 60/882,242, filed on Feb. 5, 2007.

(51) Int. Cl.
*A61B 6/00* (2006.01)

(52) U.S. Cl. ................... 600/476; 600/478; 600/479

(58) Field of Classification Search ............... None
See application file for complete search history.

(56) References Cited

U.S. PATENT DOCUMENTS

| 623,022 A | 4/1899 | Johnson |
|---|---|---|
| 2,305,462 A | 12/1942 | Wolf |
| 3,874,388 A | 4/1975 | King et al. |
| 4,175,545 A | 11/1979 | Termanini |
| 4,326,529 A | 4/1982 | Doss et al. |
| 4,445,892 A | 5/1984 | Hussein et al. |
| 4,470,407 A | 9/1984 | Hussein et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |

(Continued)

FOREIGN PATENT DOCUMENTS

DE 10028155 A1 12/2000

(Continued)

OTHER PUBLICATIONS

Avitall, A Catheter System to Ablate Atrial Fibrillation in a Sterile Pericarditis Dog Model, PACE, vol. 17, p. 774, 1994.

(Continued)

*Primary Examiner* — Long V. Le
*Assistant Examiner* — Nicholas Evoy
(74) *Attorney, Agent, or Firm* — Levine Bagade Han LLP

(57) ABSTRACT

Flow reduction hood systems are described which facilitate the visualization of tissue regions through a clear fluid. Such a system may include an imaging hood having one or more layers covering the distal opening and defines one or more apertures which control the infusion and controlled retention of the clearing fluid into the hood. In this manner, the amount of clearing fluid may be limited and the clarity of the imaging of the underlying tissue through the fluid within the hood may be maintained for relatively longer periods of time by inhibiting, delaying, or preventing the infusion of surrounding blood into the viewing field. The aperture size may be controlled to decrease or increase through selective inflation of the membrane or other mechanisms.

45 Claims, 25 Drawing Sheets

U.S. PATENT DOCUMENTS

| | | |
|---|---|---|
| 4,681,093 A | 7/1987 | Ono et al. |
| 4,709,698 A | 12/1987 | Johnston et al. |
| 4,710,192 A | 12/1987 | Liotta et al. |
| 4,727,418 A | 2/1988 | Kato et al. |
| 4,784,133 A | 11/1988 | Mackin |
| 4,848,323 A | 7/1989 | Marijnissen et al. |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,961,738 A | 10/1990 | Mackin |
| 4,976,710 A | 12/1990 | Mackin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,171,259 A | 12/1992 | Inoue |
| 5,281,238 A | 1/1994 | Chin et al. |
| 5,282,827 A | 2/1994 | Kensey et al. |
| 5,306,234 A | 4/1994 | Johnson |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wiita et al. |
| 5,348,554 A | 9/1994 | Imran et al. |
| 5,353,792 A | 10/1994 | Lubbers et al. |
| 5,370,647 A | 12/1994 | Graber et al. |
| 5,373,840 A | 12/1994 | Knighton |
| 5,375,612 A | 12/1994 | Cottenceau et al. |
| 5,385,148 A | 1/1995 | Lesh et al. |
| 5,403,326 A | 4/1995 | Harrison et al. |
| 5,405,376 A | 4/1995 | Mulier et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | LaFontaine et al. |
| 5,591,119 A | 1/1997 | Adair |
| 5,593,405 A | 1/1997 | Osypka |
| 5,593,422 A | 1/1997 | Muijs Van de Moer et al. |
| 5,593,424 A | 1/1997 | Northrup, III |
| 5,672,153 A | 9/1997 | Lax et al. |
| 5,676,693 A | 10/1997 | LaFontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,722,403 A | 3/1998 | McGee et al. |
| 5,725,523 A | 3/1998 | Mueller |
| 5,746,747 A | 5/1998 | McKeating |
| 5,749,846 A | 5/1998 | Edwards et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,827,268 A | 10/1998 | Laufer |
| 5,829,447 A | 11/1998 | Stevens et al. |
| 5,843,118 A | 12/1998 | Sepetka et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | LaFontaine et al. |
| 5,904,651 A | 5/1999 | Swanson et al. |
| 5,908,445 A | 6/1999 | Whayne et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |
| 6,012,457 A | 1/2000 | Lesh |
| 6,024,740 A | 2/2000 | Lesh et al. |
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | LaFontaine |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 | 1/2001 | LaFontaine et al. |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,270,492 B1 | 8/2001 | Sinofsky |
| 6,275,255 B1 | 8/2001 | Adair et al. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 | 11/2001 | Gambale et al. |
| 6,322,536 B1 | 11/2001 | Rosengart et al. |

| | | | | | | |
|---|---|---|---|---|---|---|
| 6,325,797 | B1 | 12/2001 | Stewart et al. | 6,755,811 | B1 | 6/2004 | Constantz |
| 6,328,727 | B1 | 12/2001 | Frazier et al. | 6,764,487 | B2 | 7/2004 | Mulier et al. |
| 6,358,247 | B1 | 3/2002 | Altman et al. | 6,771,996 | B2 | 8/2004 | Bowe et al. |
| 6,358,248 | B1 | 3/2002 | Mulier et al. | 6,773,402 | B2 | 8/2004 | Govari et al. |
| 6,375,654 | B1 | 4/2002 | McIntyre | 6,780,151 | B2 | 8/2004 | Grabover et al. |
| 6,379,345 | B1 | 4/2002 | Constantz | 6,805,128 | B1 | 10/2004 | Pless et al. |
| 6,385,476 | B1 | 5/2002 | Osadchy et al. | 6,805,129 | B1 | 10/2004 | Pless et al. |
| 6,387,043 | B1 | 5/2002 | Yoon | 6,811,562 | B1 | 11/2004 | Pless |
| 6,387,071 | B1 | 5/2002 | Constantz | 6,833,814 | B2 | 12/2004 | Gilboa et al. |
| 6,394,096 | B1 | 5/2002 | Constantz | 6,840,923 | B1 | 1/2005 | Lapcevic |
| 6,396,873 | B1 | 5/2002 | Goldstein et al. | 6,840,936 | B2 | 1/2005 | Sliwa, Jr. et al. |
| 6,398,780 | B1 | 6/2002 | Farley et al. | 6,849,073 | B2 | 2/2005 | Hoey et al. |
| 6,401,719 | B1 | 6/2002 | Farley et al. | 6,858,005 | B2 | 2/2005 | Ohline et al. |
| 6,409,722 | B1 | 6/2002 | Hoey et al. | 6,858,026 | B2 | 2/2005 | Sliwa, Jr. et al. |
| 6,416,511 | B1 | 7/2002 | Lesh et al. | 6,863,668 | B2 | 3/2005 | Gillespie et al. |
| 6,419,669 | B1 | 7/2002 | Frazier et al. | 6,866,651 | B2 | 3/2005 | Constantz |
| 6,423,051 | B1 | 7/2002 | Kaplan et al. | 6,887,237 | B2 | 5/2005 | McGaffigan |
| 6,423,055 | B1 | 7/2002 | Farr et al. | 6,892,091 | B1 | 5/2005 | Ben-Haim et al. |
| 6,423,058 | B1 | 7/2002 | Edwards et al. | 6,896,690 | B1 | 5/2005 | Lambrecht et al. |
| 6,428,536 | B2 | 8/2002 | Panescu et al. | 6,899,672 | B2 | 5/2005 | Chin et al. |
| 6,440,119 | B1 | 8/2002 | Nakada et al. | 6,915,154 | B1 | 7/2005 | Docherty et al. |
| 6,458,151 | B1 | 10/2002 | Saltiel | 6,923,805 | B1 | 8/2005 | LaFontaine et al. |
| 6,464,697 | B1 | 10/2002 | Edwards et al. | 6,929,010 | B2 | 8/2005 | Vaska et al. |
| 6,474,340 | B1 | 11/2002 | Vaska et al. | 6,932,809 | B2 | 8/2005 | Sinofsky |
| 6,475,223 | B1 | 11/2002 | Werp et al. | 6,939,348 | B2 | 9/2005 | Malecki et al. |
| 6,478,769 | B1 | 11/2002 | Parker | 6,942,657 | B2 | 9/2005 | Sinofsky et al. |
| 6,482,162 | B1 | 11/2002 | Moore | 6,949,095 | B2 | 9/2005 | Vaska et al. |
| 6,484,727 | B1 | 11/2002 | Vaska et al. | 6,953,457 | B2 | 10/2005 | Farr et al. |
| 6,485,489 | B2 | 11/2002 | Teirstein et al. | 6,955,173 | B2 | 10/2005 | Lesh |
| 6,488,671 | B1 | 12/2002 | Constantz et al. | 6,962,589 | B2 | 11/2005 | Mulier et al. |
| 6,494,902 | B2 | 12/2002 | Hoey et al. | 6,971,394 | B2 | 12/2005 | Sliwa, Jr. et al. |
| 6,497,705 | B2 | 12/2002 | Comben | 6,974,464 | B2 | 12/2005 | Quijano et al. |
| 6,500,174 | B1 | 12/2002 | Maguire et al. | 6,979,290 | B2 | 12/2005 | Mourlas et al. |
| 6,502,576 | B1 | 1/2003 | Lesh | 6,982,740 | B2 | 1/2006 | Adair et al. |
| 6,514,249 | B1 | 2/2003 | Maguire et al. | 6,984,232 | B2 | 1/2006 | Vanney et al. |
| 6,517,533 | B1 | 2/2003 | Swaminathan | 6,994,094 | B2 | 2/2006 | Schwartz |
| 6,527,979 | B2 | 3/2003 | Constantz et al. | 7,019,610 | B2 | 3/2006 | Creighton, IV et al. |
| 6,532,380 | B1 | 3/2003 | Close et al. | 7,025,746 | B2 | 4/2006 | Tal |
| 6,533,767 | B2 | 3/2003 | Johansson et al. | 7,030,904 | B2 | 4/2006 | Adair et al. |
| 6,537,272 | B2 | 3/2003 | Christopherson et al. | 7,041,098 | B2 | 5/2006 | Farley et al. |
| 6,540,733 | B2 | 4/2003 | Constantz et al. | 7,042,487 | B2 | 5/2006 | Nakashima |
| 6,540,744 | B2 | 4/2003 | Hassett et al. | 7,044,135 | B2 | 5/2006 | Lesh |
| 6,544,195 | B2 | 4/2003 | Wilson et al. | 7,052,493 | B2 | 5/2006 | Vaska et al. |
| 6,547,780 | B1 | 4/2003 | Sinofsky | 7,090,683 | B2 | 8/2006 | Brock et al. |
| 6,558,375 | B1 | 5/2003 | Sinofsky et al. | 7,118,566 | B2 | 10/2006 | Jahns |
| 6,562,020 | B1 | 5/2003 | Constantz et al. | 7,156,845 | B2 | 1/2007 | Mulier et al. |
| 6,572,609 | B1 | 6/2003 | Farr et al. | 7,163,534 | B2 | 1/2007 | Brucker et al. |
| 6,579,285 | B2 | 6/2003 | Sinofsky | 7,166,537 | B2 | 1/2007 | Jacobsen et al. |
| 6,585,732 | B2 | 7/2003 | Mulier et al. | 7,169,144 | B2 | 1/2007 | Hoey et al. |
| 6,587,709 | B2 | 7/2003 | Solf et al. | 7,186,214 | B2 | 3/2007 | Ness |
| 6,593,884 | B1 | 7/2003 | Gilboa et al. | 7,207,984 | B2 | 4/2007 | Farr et al. |
| 6,605,055 | B1 | 8/2003 | Sinofsky et al. | 7,217,268 | B2 | 5/2007 | Eggers et al. |
| 6,613,062 | B1 | 9/2003 | Leckrone et al. | 7,242,832 | B2 | 7/2007 | Carlin et al. |
| 6,622,732 | B2 | 9/2003 | Constantz | 7,247,155 | B2 | 7/2007 | Hoey et al. |
| 6,626,855 | B1 | 9/2003 | Weng et al. | 7,261,711 | B2 | 8/2007 | Mulier et al. |
| 6,626,900 | B1 | 9/2003 | Sinofsky et al. | 7,263,397 | B2 | 8/2007 | Hauck et al. |
| 6,635,070 | B2 | 10/2003 | Leeflang et al. | 7,276,061 | B2 | 10/2007 | Schaer et al. |
| 6,645,202 | B1 | 11/2003 | Pless et al. | 7,309,328 | B2 | 12/2007 | Kaplan et al. |
| 6,650,923 | B1 | 11/2003 | Lesh et al. | 7,435,248 | B2 | 10/2008 | Taimisto et al. |
| 6,658,279 | B2 | 12/2003 | Swanson et al. | 7,527,625 | B2 | 5/2009 | Knight et al. |
| 6,659,940 | B2 | 12/2003 | Adler | 7,534,204 | B2 | 5/2009 | Starksen et al. |
| 6,673,090 | B2 | 1/2004 | Root et al. | 7,569,052 | B2 | 8/2009 | Phan et al. |
| 6,676,656 | B2 | 1/2004 | Sinofsky | 7,736,347 | B2 | 6/2010 | Kaplan et al. |
| 6,679,836 | B2 | 1/2004 | Couvillon, Jr. | 7,758,499 | B2 | 7/2010 | Adler |
| 6,682,526 | B1 | 1/2004 | Jones et al. | 7,860,555 | B2 | 12/2010 | Saadat |
| 6,689,128 | B2 | 2/2004 | Sliwa, Jr. et al. | 7,860,556 | B2 | 12/2010 | Saadat |
| 6,692,430 | B2 | 2/2004 | Adler | 2001/0005789 | A1 | 6/2001 | Root et al. |
| 6,701,581 | B2 | 3/2004 | Senovich et al. | 2001/0020126 | A1 | 9/2001 | Swanson et al. |
| 6,701,931 | B2 | 3/2004 | Sliwa, Jr. et al. | 2001/0031912 | A1 | 10/2001 | Adler |
| 6,702,780 | B1 | 3/2004 | Gilboa et al. | 2001/0039416 | A1 | 11/2001 | Moorman et al. |
| 6,704,043 | B2 | 3/2004 | Goldstein et al. | 2001/0047136 | A1 | 11/2001 | Domanik et al. |
| 6,706,039 | B2 | 3/2004 | Mulier et al. | 2001/0047184 | A1 | 11/2001 | Connors |
| 6,712,798 | B2 | 3/2004 | Constantz | 2001/0052930 | A1 | 12/2001 | Adair et al. |
| 6,719,747 | B2 | 4/2004 | Constantz et al. | 2002/0004644 | A1 | 1/2002 | Koblish |
| 6,719,755 | B2 | 4/2004 | Sliwa, Jr. et al. | 2002/0026145 | A1 | 2/2002 | Bagaoisan et al. |
| 6,730,063 | B2 | 5/2004 | Delaney et al. | 2002/0065455 | A1 | 5/2002 | Ben-Haim et al. |
| 6,736,810 | B2 | 5/2004 | Hoey et al. | 2002/0068853 | A1 | 6/2002 | Adler et al. |
| 6,751,492 | B2 | 6/2004 | Ben-Haim | 2002/0080248 | A1 | 6/2002 | Adair et al. |
| 6,755,790 | B2 | 6/2004 | Stewart et al. | 2002/0087166 | A1 | 7/2002 | Brock et al. |

| | | |
|---|---|---|
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0165598 A1 | 11/2002 | Wahr et al. |
| 2002/0169377 A1 | 11/2002 | Khairkhahan et al. |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0216720 A1 | 11/2003 | Sinofsky |
| 2003/0220574 A1 | 11/2003 | Markus et al. |
| 2003/0222325 A1 | 12/2003 | Jacobsen et al. |
| 2004/0006333 A1 | 1/2004 | Arnold et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler |
| 2004/0097788 A1 | 5/2004 | Mourlas et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215183 A1 | 10/2004 | Hoey et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 | 6/2005 | Starksen et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0158899 A1 | 7/2005 | Jacobsen et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0182465 A1 | 8/2005 | Ness |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1 | 2/2006 | Knight et al. |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0184048 A1 | 8/2006 | Saadat |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033290 A1 | 2/2008 | Saadat et al. |
| 2008/0057106 A1 | 3/2008 | Erickson et al. |
| 2008/0058590 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0076498 A1 | 3/2009 | Saadat et al. |
| 2009/0143640 A1 | 6/2009 | Saadat et al. |
| 2009/0264727 A1 | 10/2009 | Markowitz et al. |
| 2009/0267773 A1 | 10/2009 | Markowitz et al. |
| 2010/0004506 A1 | 1/2010 | Saadat |
| 2010/0004661 A1 | 1/2010 | Verin et al. |
| 2011/0060227 A1 | 3/2011 | Saadat |
| 2011/0060298 A1 | 3/2011 | Saadat |
| 2011/0144576 A1 | 6/2011 | Rothe et al. |

FOREIGN PATENT DOCUMENTS

| | | |
|---|---|---|
| EP | 0283661 | 9/1988 |
| EP | 0301288 A1 | 2/1999 |
| JP | 59093413 A | 5/1984 |
| JP | 59-181315 | 10/1984 |

| | | |
|---|---|---|
| JP | 01-221133 | 9/1989 |
| JP | 03-284265 | 12/1991 |
| JP | 05-103746 | 4/1993 |
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 98/18388 | 5/1998 |
| WO | WO 03/039350 | 5/2003 |
| WO | WO 03/053491 | 7/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

Avitall, Right-Sided Driven Atrial Fibrillation in a Sterile Pericarditis Dog Model, PACE, vol. 17, p. 774, 1994.
Avitall, Vagally Mediated Atrial Fibrillation in a Dog Model can be Ablated by Placing Linear Radiofrequency Lesions at the Junction of the Right Atrial Appendage and the Superior Vena Cava, PACE, vol. 18, p. 857, 1995.
Baker, Nonpharmacologic Approaches to the Treatment of Atrial Fibrillation and Atrial Flutter, J. Cardiovasc. Electrophysiol., vol. 6, pp. 972-978, 1995.
Bhakta, Principles of Electroanatomic Mapping, Indian Pacing & Electrophysiol J., vol. 8, No. 1, pp. 32-50, 2008.
Bidoggia, Transseptal Left Heart Catheterization: Usefulness of the Intracavitary Electrocardiogram in the Localization of the Fossa Ovalis, Cathet Cardiovasc Diagn., vol. 24, No. 3, pp. 221-225, 1991.
Bredikis, Surgery of Tachyarrhythmia: Intracardiac Closed Heart Cryoablation, PACE, vol. 13, pp. 1980-1984, 1990.
Cox, Cardiac Surgery for Arrhythmias, J. Cardiovasc. Electrophysiol., vol. 15, pp. 250-262, 2004.
Cox, Five-Year Experience With the Maze Procedure for Atrial Fibrillation, Ann. Thorac. Surg., vol. 56, pp. 814-824, 1993.
Cox, Modification of the Maze Procedure for Atrial Flutter and Atrial Fibrillation, J. Thorac. Cardiovasc. Surg., vol. 110, pp. 473-484, 1995.
Cox, The Status of Surgery for Cardiac Arrhythmias, Circulation, vol. 71, pp. 413-417, 1985.
Cox, The Surgical Treatment of Atrial Fibrillation, J. Thorac Cardiovasc. Surg., vol. 101, pp. 584-592, 1991.
Elvan, Replication of the "Maze" Procedure by Radiofrequency Catheter Ablation Reduces the Ability to Induce Atrial Fibrillation, PACE, vol. 17, p. 774, 1994.
Elvan, Radiofrequency Catheter Ablation (RFCA) of the Atria Effectively Abolishes Pacing Induced Chronic Atrial Fibrillation, PACE, vol. 18, p. 856, 1995.
Elvan, Radiofrequency Catheter Ablation of the Atria Reduces Inducibility and Duration of Atrial Fibrillation in Dogs, Circulation, vol. 91, pp. 2235-2244, 1995.
European Patent Application No. 06734083.6 filed Jan. 30, 2006 in the name of Saadat et al., extended European Search Report mailed Jul. 1, 2009.
European Patent Application No. 06734083.6 filed Jan. 30, 2006 in the name of Saadat et al., office action mailed Oct. 23, 2009.
Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.
Hoey, Intramural Ablation Using Radiofrequency Energy Via Screw-Tip Catheter and Saline Electrode, PACE, vol. 18, p. 487, 1995.
Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, CHEST, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist: Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/828,267, filed Jul. 25, 2007 in the name of Saadat et al., Non-final Office Action mailed Jan. 14, 2010.
U.S. Appl. No. 12/117,655, filed May 8, 2008 in the name of Saadat et al., Non-final Office Action mailed Jun. 8, 2009.
Willkampf, Radiofrequency Ablation with a Cooled Porous Electrode Catheter, JACC, vol. 11, No. 2, p. 17A, 1988.
European Patent Application No. 06734083.6 filed Jan. 30, 2006 in the name of Saadat et al., Examination Communication mailed May 18, 2010.
European Patent Application No. 07841754.0 filed Aug. 31 2007 in the name of Saadat et al., Supplemental European Search Report mailed Jun. 30, 2010.
European Patent Application No. 08746822.9 filed Apr. 24, 2008 in the name of Rothe et al., European Search Resort mailed Mar. 29, 2010.
European Patent Application No. 08746822.9 filed Apr. 24, 2008 in the name of Rothe et al., Office Action mailed Jul. 13, 2010.
U.S. Appl. No. 11/259,498, filed Oct. 25, 2005 in the name of Saadat et al., Non-final Office Action mailed Feb. 25, 2010.
U.S. Appl. No. 11/560,742, filed Nov. 16, 2006 in the name of Saadat, Non-final Office Action mailed Jun. 10, 2010.
U.S. Appl. No. 11/687,597, filed Mar. 16, 2007 in the name of Saadat et al., Non-final Office Action mailed Jul 21, 2010.
U.S. Appl. No. 12/117,655, filed May 8, 2008 in the name of Peh et al., Final Office Action mailed Mar. 1, 2010.
U.S. Appl. No. 61/286,283, filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Future Publishing Co., Armonk, NY.
U.S. Appl. No. 11/775,771, filed Jul. 10, 2007 in the name of Saadat et al., Non-final Office Action mailed Aug. 27, 2010.
U.S. Appl. No. 11/828,267, filed Jul. 25, 2007 in the name of Saadat et al., final Office Action mailed Sep. 16, 2010.
U.S. Appl. No. 11/259,498, filed Oct. 25, 2005 in the name of Saadat, Notice of Allowance mailed Nov. 15, 2010.
U.S. Appl. No. 11/560,742, filed Nov. 16, 2006 in the name of Saadat, Notice of Allowance mailed Nov. 15, 2010.
U.S. Appl. No. 12/464,800, filed May 12, 2009 in the name of Peh et al., non-final Office Action mailed Nov. 24, 2010.
U.S. Appl. No. 11/560,732, filed Nov. 16, 2006 in the name of Saadat, Notice of Allowance mailed Feb. 3, 2011.
U.S. Appl. No. 11/848,429, filed Aug. 31, 2007 in the name of Peh et al., non-final Office Action mailed Nov. 24, 2010.
European Patent Application No. 07812146.4 filed Jun. 14, 2007 in the name of Voyage Medical, Inc., European Search Report mailed Nov. 18, 2010.
European Patent Application No. 07799466.3 filed Jul. 10, 2007 in the name of Voyage Medical, Inc., European Search Report mailed Nov. 18, 2010.

U.S. Appl. No. 12/117,655, filed May 8, 2008 in the name of Peh et al., non-final Office Action mailed Dec. 16, 2010.
European Patent Application No. 06734083.6 filed Jan. 30, 2006 in the name of Voyage Medical, Inc., Office Action mailed Nov. 12, 2010.
U.S. Appl. No. 12/947,198, filed Nov. 16, 2010 in the name of Saadat, non-final Office Action mailed Feb. 18, 2011.
U.S. Appl. No. 12/947,246, filed Nov. 16, 2006 in the name of Saadat, Notice of Allowance mailed Feb. 18, 2011.
U.S. Appl. No. 11/687,597, filed Mar. 16, 2007 in the name of Saadat, Notice of Allowance mailed Feb. 24, 2011.
U.S. Appl. No. 11/560,732, filed Mar. 16, 2007 in the name of Saadat, Notice of Allowance mailed Feb. 24, 2011.
U.S. Appl. No. 11/848,207, filed Aug. 30, 2007 in the name of Saadat et al., non-final Office Action mailed Feb. 25, 2011.
Japanese Patent Application No. 2007-554156 filed Jan. 30, 2006 in the name of Voyage Medical, Inc., Office Action mailed Feb. 15, 2011.
European Patent Application No. 07758716.0 filed Mar. 16, 2007 in the name of Voyage Medical, Inc., Supplemental European Search Report mailed Feb. 28, 2011.
U.S. Appl. No. 11/848,202, filed Aug. 30, 2007 in the name of Saadat et al., non-final Office Action mailed Mar. 11, 2011.
U.S. Appl. No. 11/763,399, filed Jun. 14, 2007 in the name of Saadat et al., non-final Office Action mailed Apr. 11, 2011.
U.S. Appl. No. 12/499,011, filed Jul. 7, 2009 in the name of Rothe et al., non-final Office Action mailed Apr. 12, 2011.
U.S. Appl. No. 12/367,019, filed Feb. 6, 2009 in the name of Miller et al., non-final Office Action mailed Apr. 22, 2011.
U.S. Appl. No. 11/959,158, filed Dec. 18, 2007 in the name of Saadat et al., non-final Office Action mailed Apr. 25, 2011.
U.S. Appl. No. 11/848,532, filed Aug. 31, 2007 in the name of Saadat et al., non-final Office Action mailed Apr. 26, 2011.
U.S. Appl. No. 11/828,281, filed Jul. 25, 2007 in the name of Peh et al., non-final Office Action mailed Apr. 27, 2011.
U.S. Appl. No. 11/961,950, filed Dec. 20, 2007 in the name of Saadat et al., non-final Office Action mailed May 9, 2011.
U.S. Appl. No. 11/961,995, filed Dec. 20, 2007 in the name of Saadat et al., non-final Office Action mailed May 9, 2011.
U.S. Appl. No. 11/962,029, filed Dec. 20, 2007 in the name of Saadat et al., non-final Office Action mailed May 9, 2011.
U.S. Appl. No. 11/828,267, filed Jul. 25, 2007 in the name of Saadat et al., non-final Office Action mailed May 11, 2011.
Japanese Patent Application No. 2009-500630 filed Mar. 16, 2007 in the name of Voyage Medical, Inc., Office Action mailed Apr. 27, 2011.
U.S. Appl. No. 11/775,771, filed Jul. 10, 2007 in the name of Saadat et al., final Office Action mailed May 12, 2011.
U.S. Appl. No. 11/877,386, filed Oct. 23, 2007 in the name of Saadat et al., non-final Office Action mailed May 20, 2011.
U.S. Appl. No. 11/775,819, filed Jul. 10, 2007 in the name of Saadat et al., non-final Office Action mailed May 20, 2011.
U.S. Appl. No. 11/775,837, filed Jul. 10, 2007 in the name of Saadat et al., non-final Office Action mailed May 23, 2011.
U.S. Appl. No. 12/117,655, filed May 8, 2008 in the name of Peh et al., final Office Action mailed Jun. 2, 2011.
U.S. Appl. No. 12/323,281, filed Nov. 25, 2008 in the name of Saadat et al., non-final Office Action mailed Jun. 7, 2011.
Japanese Patent Application No. 2007-554156 filed Jan. 30, 2006 in the name of Voyage Medical, Inc., Notice of Allowance mailed Jun. 13, 2011.

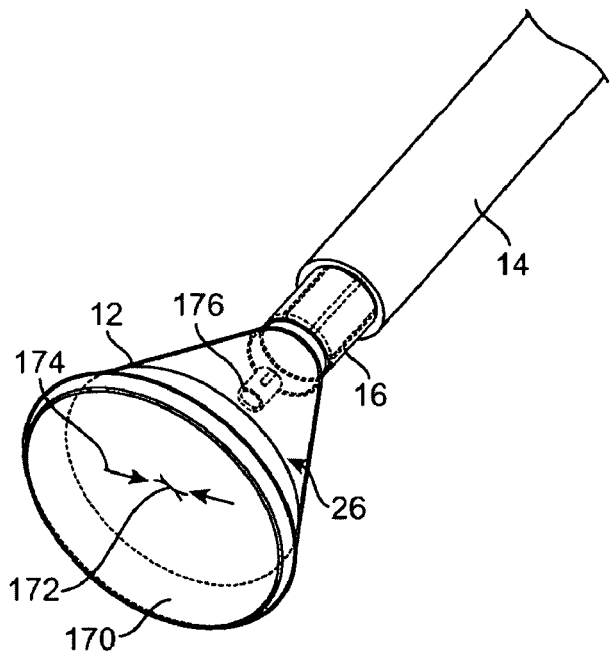 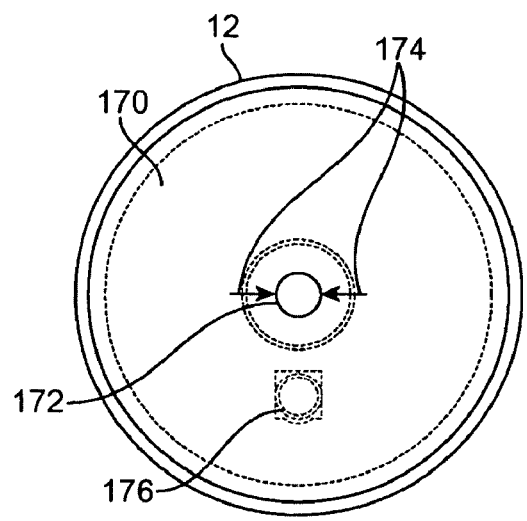
FIG. 11A       FIG. 11B
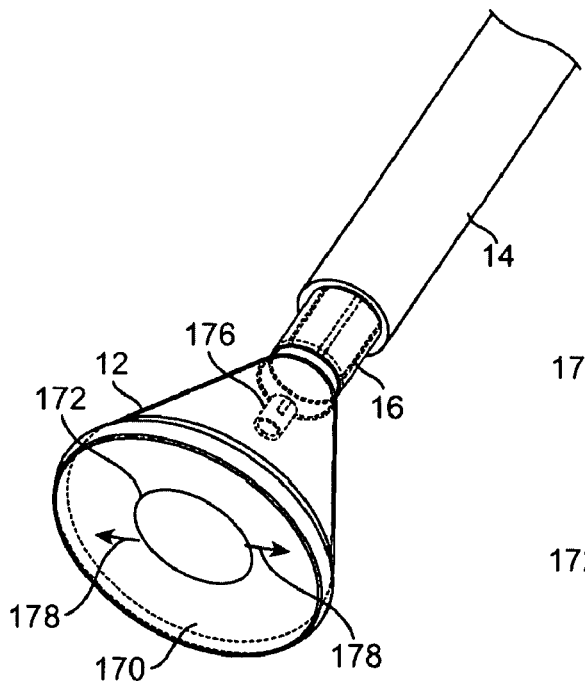 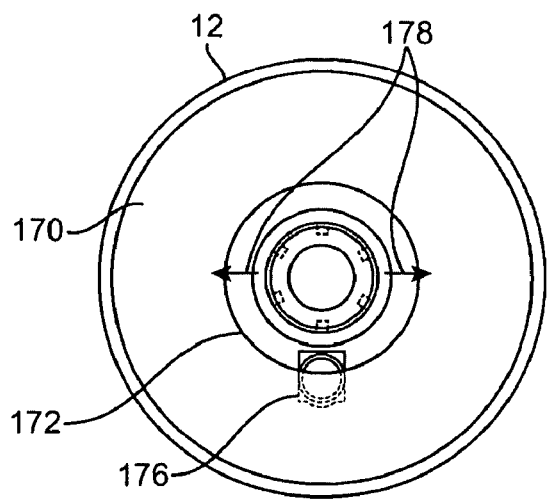
FIG. 12A       FIG. 12B

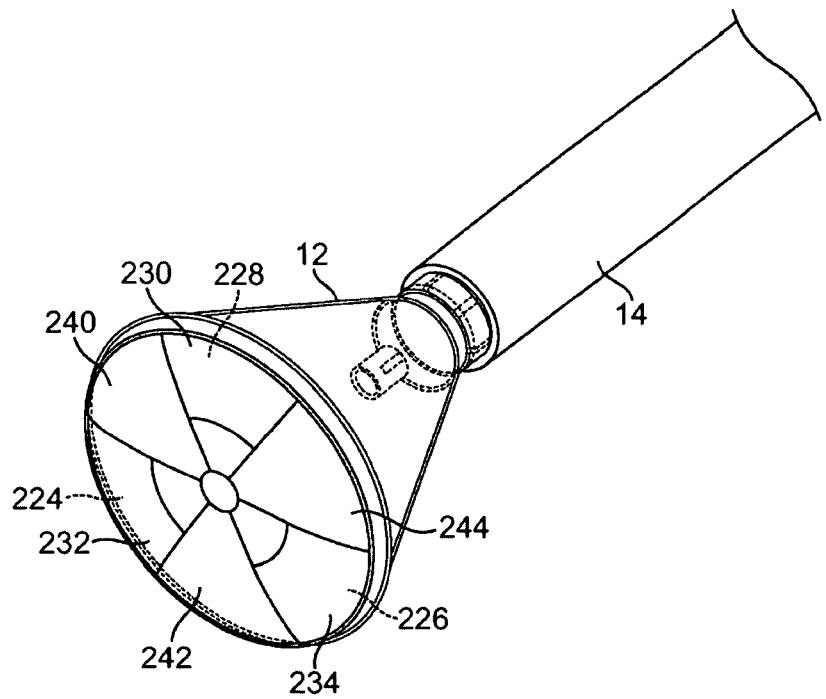
FIG. 21
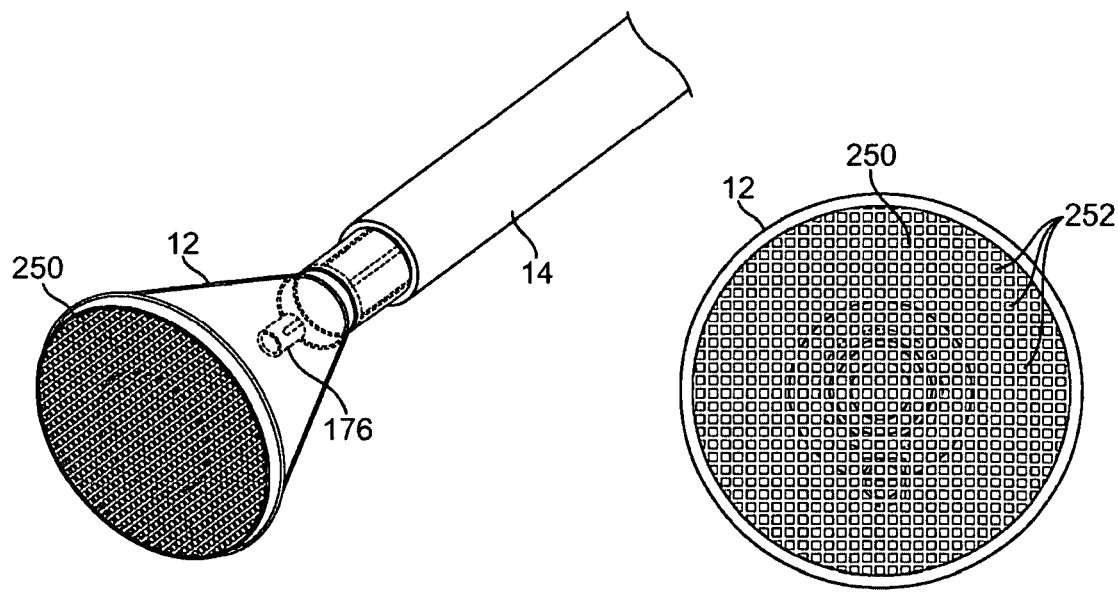
FIG. 22A
FIG. 22B

FLOW REDUCTION HOOD SYSTEMS

CROSS-REFERENCE TO RELATED APPLICATIONS

This application claims the benefit of priority to U.S. Prov. Pat. App. 60/888,242 filed Feb. 5, 2007 and is also a continuation-in-part of U.S. patent application Ser. No. 11/259,498 filed Oct. 25, 2005 (now U.S. Pat. No. 7,860,555), each of which is incorporated herein by reference in its entirety.

FIELD OF THE INVENTION

The present invention relates generally to medical devices used for accessing, visualizing, and/or treating regions of tissue within a body. More particularly, the present invention relates to flow reduction hood systems for accessing, visualizing, and/or treating tissue regions with devices that are configured to facilitate visualization of the tissue.

BACKGROUND OF THE INVENTION

Conventional devices for accessing and visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Moreover, many of the conventional imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. No. 5,895,417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion desired.

Conventional accompanying imaging devices, such as fluoroscopy, are unable to detect perpendicular electrode orientation, catheter movement during the cardiac cycle, and image catheter position throughout lesion formation. Without real-time visualization, it is difficult to reposition devices to another area that requires transmural lesion ablation. The absence of real-time visualization also poses the risk of incorrect placement and ablation of critical structures such as sinus node tissue which can lead to fatal consequences.

Thus, a tissue imaging system which is able to provide real-time in vivo access to and images of tissue regions within body lumens such as the heart through opaque media such as blood and which also provides instruments for therapeutic procedures are desirable.

BRIEF SUMMARY OF THE INVENTION

The tissue-imaging apparatus described relates to variations of a device and/or method to provide real-time images in vivo of tissue regions within a body lumen such as a heart, which is filled with blood flowing dynamically therethrough. Such an apparatus may be utilized for many procedures, e.g., mitral valvuloplasty, left atrial appendage closure, arrhythmia ablation, transseptal access and patent foramen ovale closure among other procedures. Further details of such a visualization catheter and methods of use are shown and described in U.S. Pat. Pub. 2006/0184048 A1, which is incorporated herein by reference in its entirety.

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or electronic imaging assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The visualization catheter may also have one or more membranes or layers of a polymeric material which covers at least a portion of the open area. The membrane or layer may be an extension of the deployed hood or it may be a separate structure. In either case, the membrane or layer may define at least one opening which allows for fluid communication between the visualization hood and the fluid environment within which the catheter is immersed.

In operation, after the imaging hood has been deployed, fluid may be pumped at a positive pressure through the fluid delivery lumen until the fluid fills the open area completely and displaces any blood from within the open area. When the hood and membrane or layer is pressed against the tissue region to be visualized or treated, the contact between the one or more openings and the tissue surface may help to retain the clear fluid within the hood for visualization. Moreover, the membrane or layer may help to retain the fluid within the hood while also minimizing any fluid leakage therefrom. Additionally, the one or more openings may also provide for direct access to the underlying tissue region to be treated by any number of tools or instruments positioned within the hood.

The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be deployed into an expanded shape and retracted within a catheter utilizing various mechanisms. Moreover, the imaging element, such as a CCD/CMOS imaging camera, may be positioned distally or proximally of the imaging hood when collapsed into its low-profile configuration. Such a configuration may reduce or eliminate friction during deployment and retraction as well as increase the available space within the catheter not only for the imaging unit but also for the hood.

In further controlling the flow of the purging fluid within the hood, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood may be maintained for relatively longer periods of time by inhibiting, delaying, or preventing the infusion of surrounding blood into the viewing field.

One variation for controlling the flow of the purging fluid within and from the hood may include a distensible and/or inflatable membrane which extends over the distal opening of the hood to at least partially enclose the open area or field with an aperture defined along the membrane. The aperture may be controlled to decrease or increase in size via a number of mechanisms to control the fluid rate therethrough. For instance, the aperture may be controlled by the inflation or deflation of the membrane extending over the hood opening. Other variations may utilize a membrane which is retractable over the hood to control aperture size.

Other variations may include aperture openings having other configurations such as an aperture which is slotted transversely relative to the catheter. Such a slotted aperture may extend along the entire length of the diameter of the membrane or just along a portion thereof to facilitate access of an instrument, e.g., ablation instrument, to the underlying visualized tissue. Moreover, the aperture may also function, e.g., as a template for ablation probes to create linear ablation lesions on the contacted tissue by following the slotted aperture as well as restricting or inhibiting the flow of the purging fluid from the hood. Other variations for aperture configuration may include one or more slotted openings which extend in an arcuate or curved manner over the covering or membrane. Yet another variation may include a meshed membrane or covering over the distal opening of the hood.

Other variations for controlling fluid flow may also include a plurality of inflatable elongate strips or barriers which extend over the opening of the hood adjacent to one another such that the entire distal opening of the hood may be closed by inflation or expansion of these strips or barriers. Yet another variation may comprise a rotatable barrier which may pivot or rotate relative to one or more stationary segments which are non-moving relative to the hood to transition between an open and closed configuration. By rotating the barrier, segmented openings may be formed between each respective adjacent segment. By fully rotating the barrier, the segmented openings may be fully opened and the size of the segmented openings formed can thus be controlled by rotating the barrier accordingly.

In collapsing and/or deploying a hood having a flow-control aperture, one variation for collapsing such an assembly may include use of a dilating instrument which may be advanced through the hood to engage the aperture. As the dilator is pushed further distally, the support struts supporting the hood may become straightened relative to the dilator and collapsed into a low-profile configuration. With this variation, the hood may be collapsed for delivery without having to retract the hood into a catheter sheath. Additionally, with the ability to collapse the hood distally rather than proximally, the projecting tip of the dilator may be used to actively dilate tissue openings, cavities, flaps, etc. such as the fossa ovalis or the coronary sinus.

BRIEF DESCRIPTION OF THE DRAWINGS

FIGS. 11A and 11B show perspective and end views, respectively, of a variation of the tissue visualization catheter having an aperture defined along the hood which may be narrowed or closed via an inflatable membrane.

FIGS. 12A and 12B show perspective and end views, respectively, of another variation where the aperture size may be increased upon deflation and/or depressurizing of the inflatable membrane.

FIG. 21 shows a perspective view of the catheter of FIG. 20A having the slotted openings rotated into a fully opened configuration.

FIGS. 22A and 22B show perspective and end views, respectively, of yet another variation having a meshed frame over the distal end of the hood.

DETAILED DESCRIPTION OF THE INVENTION

A tissue-imaging and manipulation apparatus described below is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures. Further examples of tissue visualization catheters which may be utilized are shown and described in further detail in U.S. patent application Ser. No. 11/259,498 filed Oct. 25, 2005, which has been incorporated hereinabove by reference in its entirety.

Figure 1A:
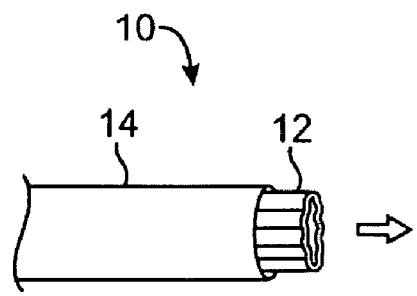
FIG. 1A shows a side view of one variation of a tissue imaging apparatus during deployment from a sheath or delivery catheter.
Figure 1B:
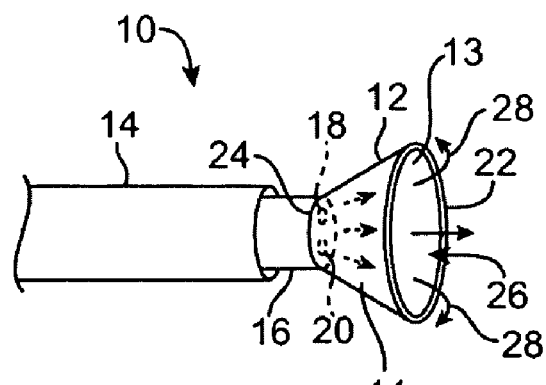
FIG. 1B shows the deployed tissue imaging apparatus of FIG. 1A having an optionally expandable hood or sheath attached to an imaging and/or diagnostic catheter.
Figure 1C:
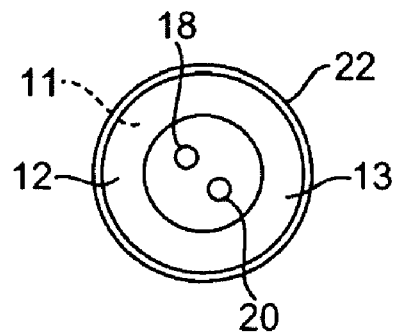
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging use. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
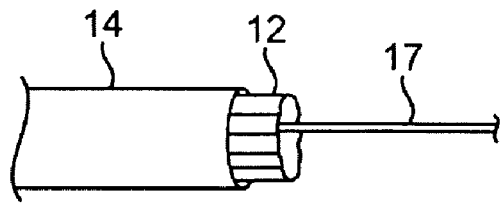
FIGS. 1D to 1F show the apparatus of FIGS. 1A to 1C with an additional lumen, e.g., for passage of a guidewire therethrough.
Figure 1E:
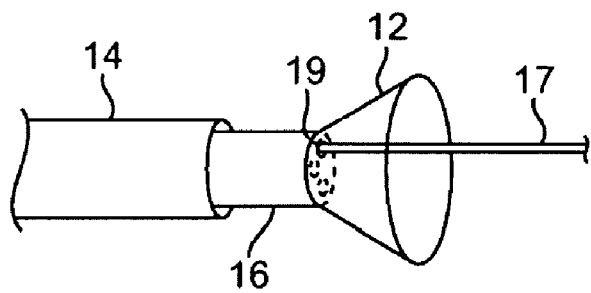
Figure 1F:
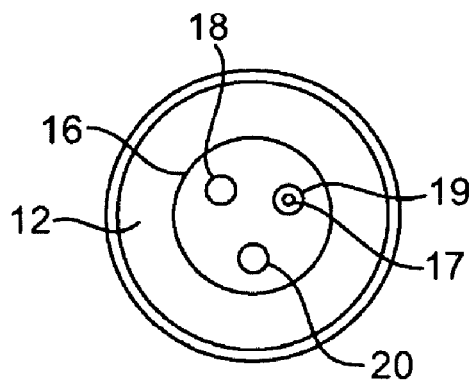

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
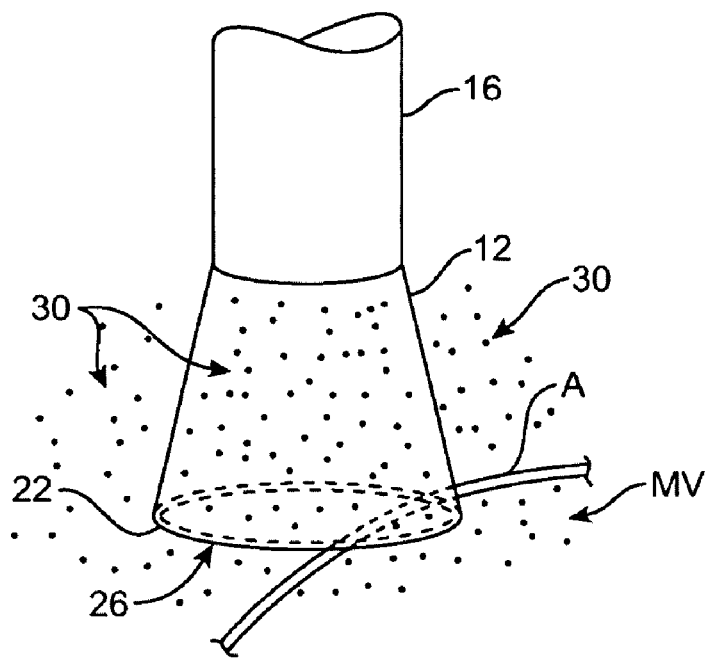
FIGS. 2A and 2B show one example of a deployed tissue imager positioned against or adjacent to the tissue to be imaged and a flow of fluid, such as saline, displacing blood from within the expandable hood.
Figure 2B:
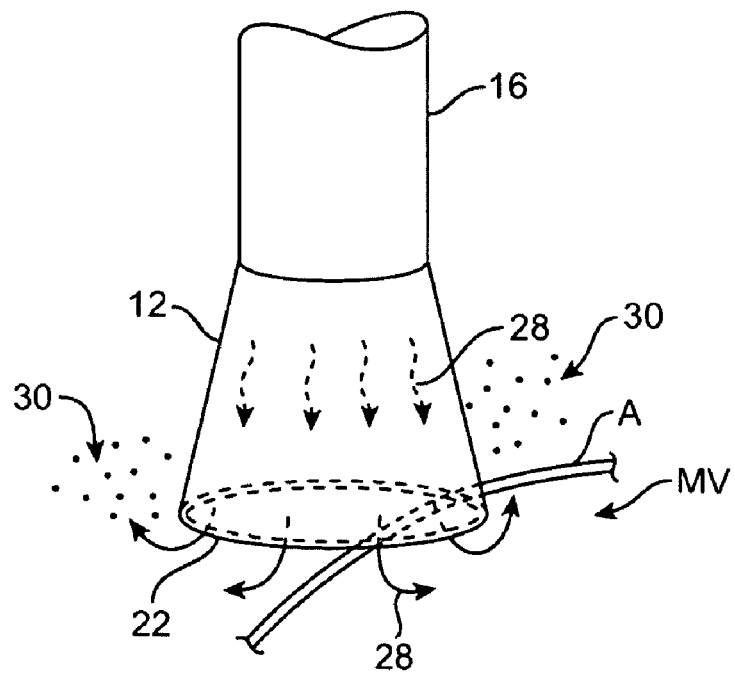

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
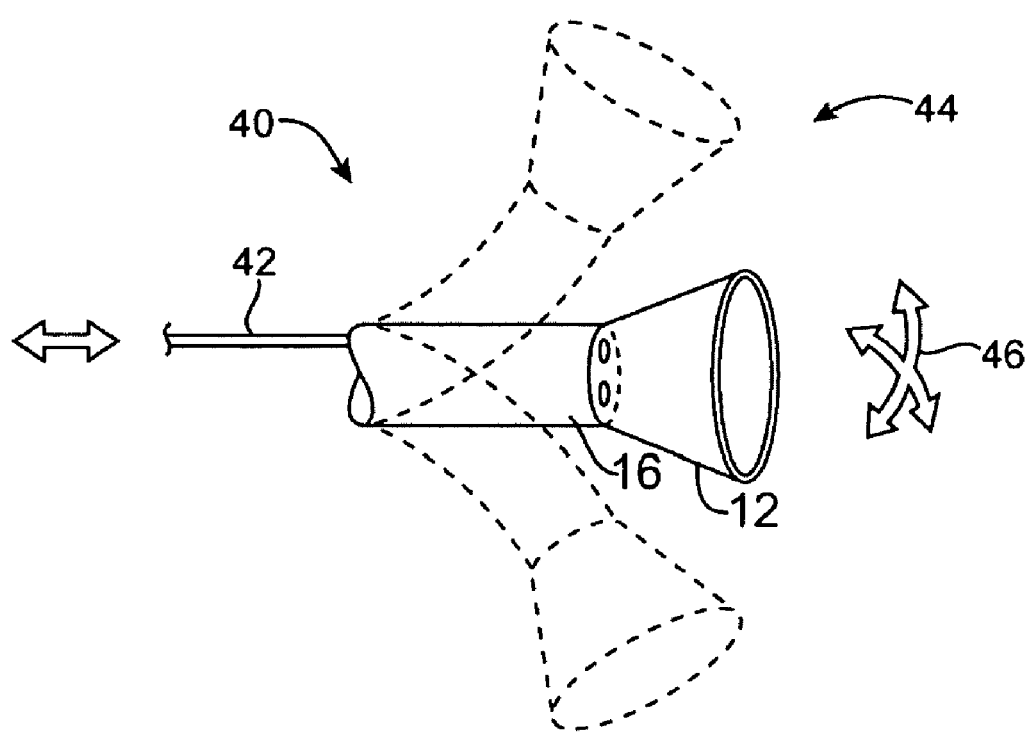
FIG. 3A shows an articulatable imaging assembly which may be manipulated via push-pull wires or by computer control.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3B:
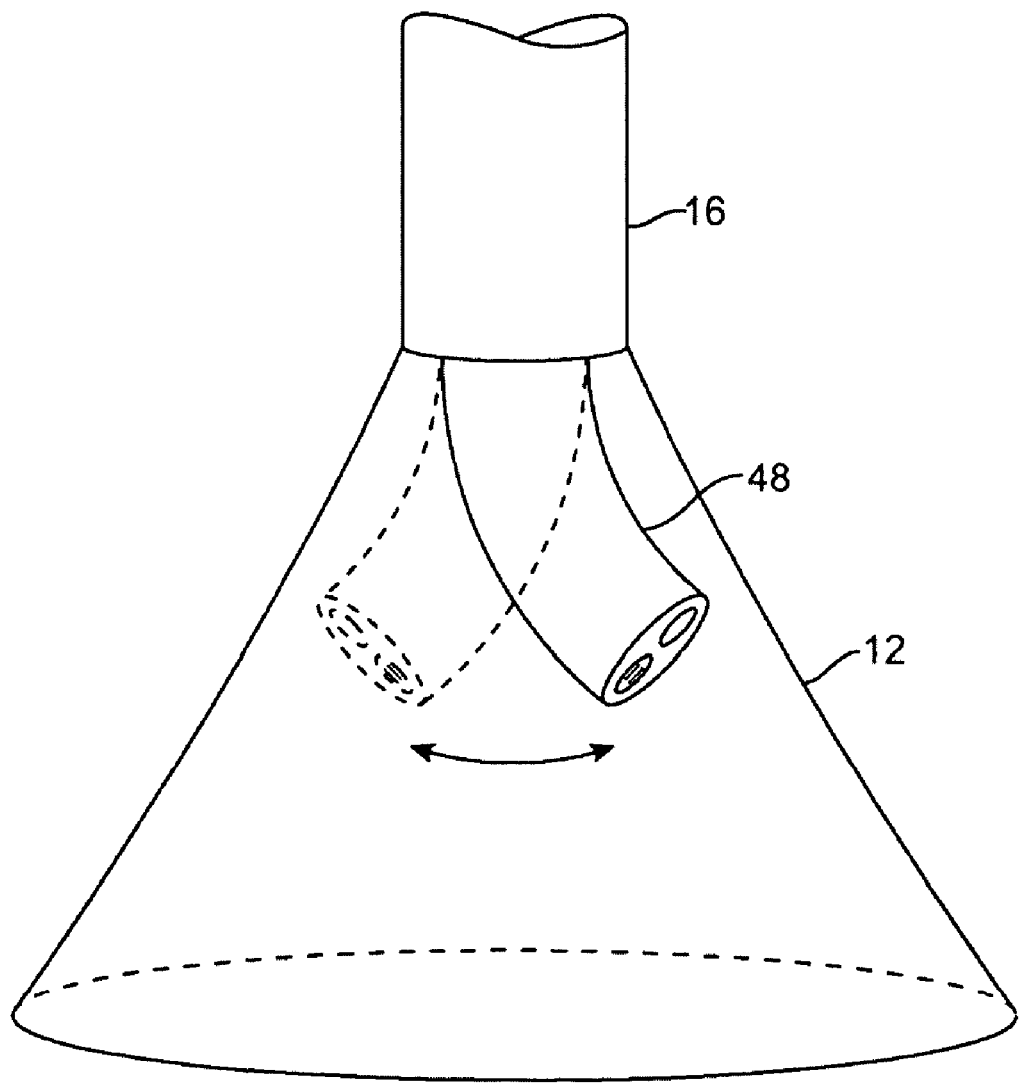
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
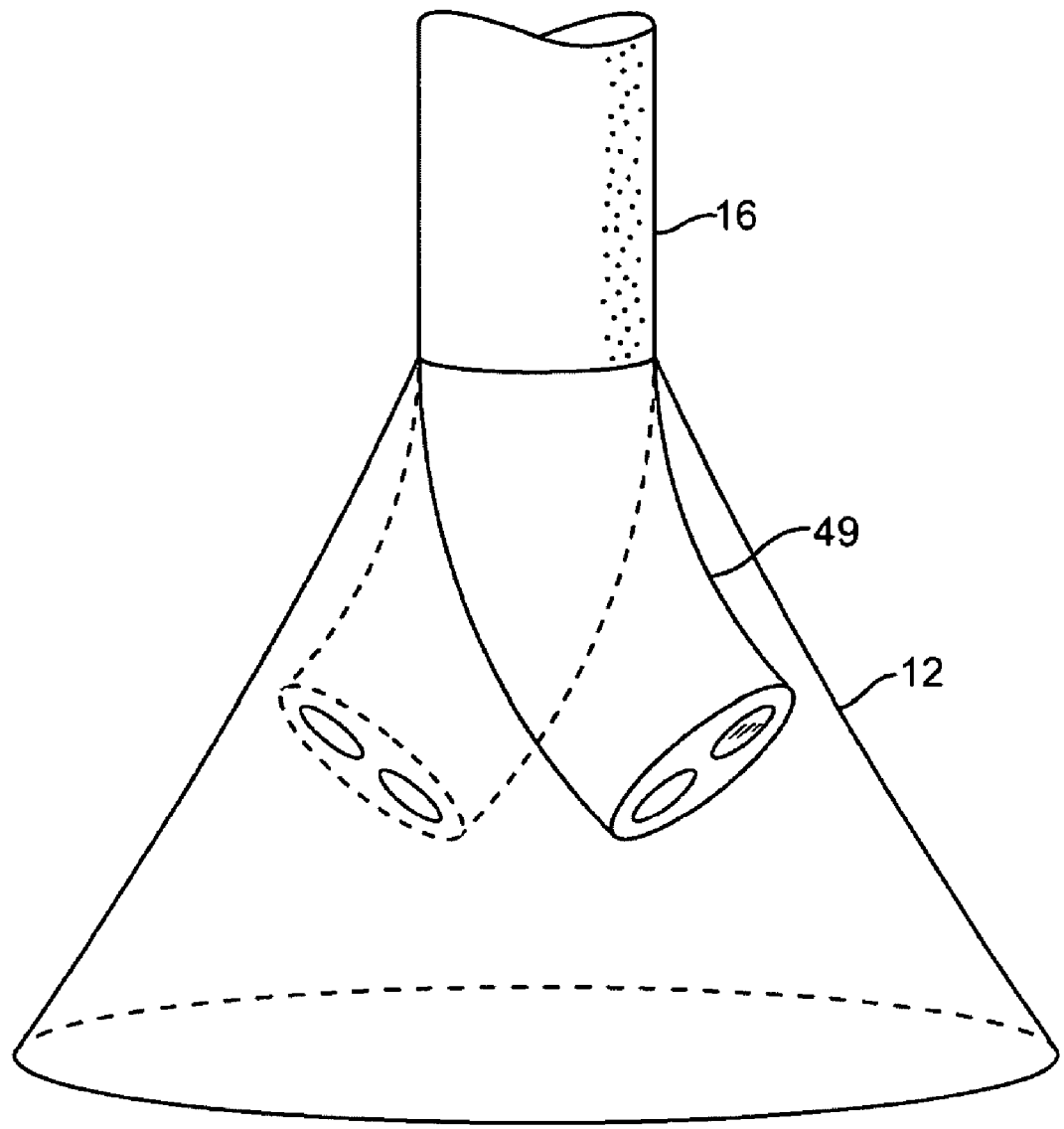

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
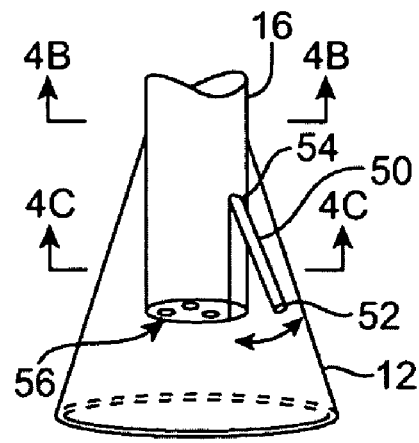
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52. e.g., a CCD or CMOS imager or optical fiber, attached at its distal end with its proximal end connected to deployment catheter 16 via a pivoting connection 54.

Figure 4B:
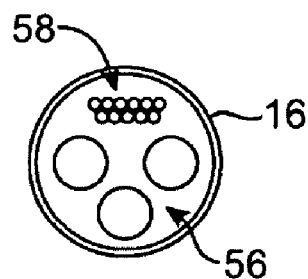
Figure 4C:
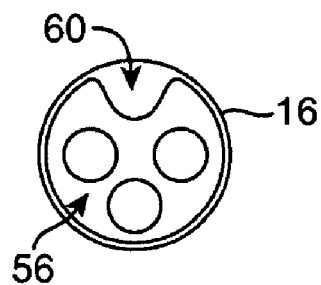

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 4D:
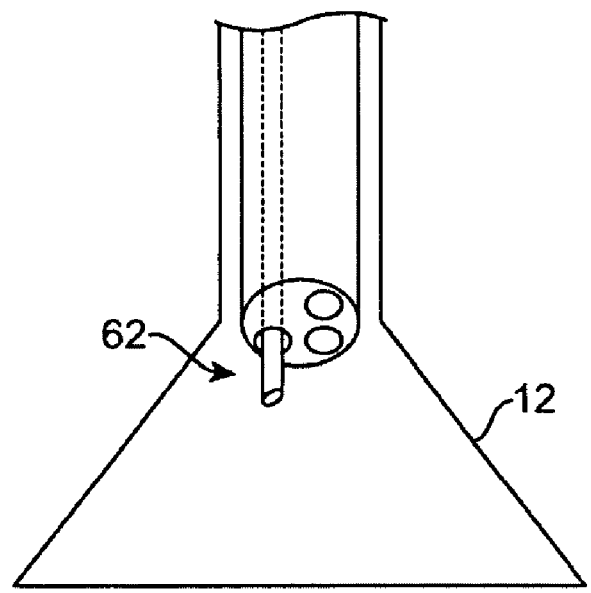
FIGS. 4D and 4E show examples of various visualization imagers which may be utilized within or along the imaging hood.
Figure 4E:
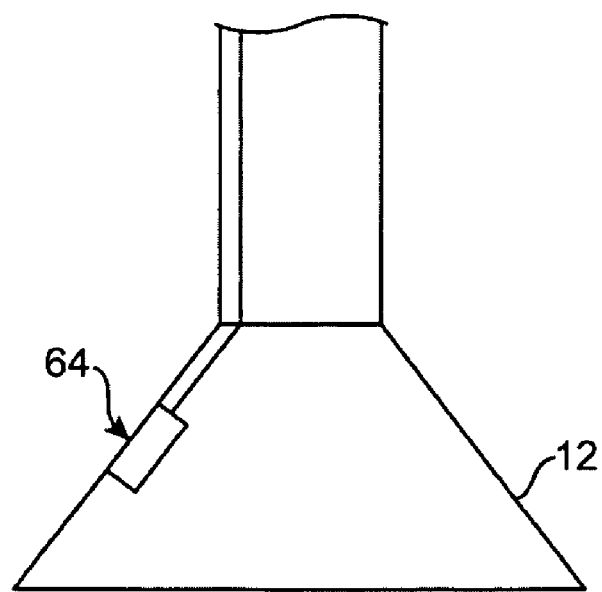

FIG. 4D shows a partial cross-sectional view of an example where one or more optical fiber bundles 62 may be positioned within the catheter and within imaging hood 12 to provide direct in-line imaging of the open area within hood 12. FIG. 4E shows another example where an imaging element 64 (e.g., CCD or CMOS electronic imager) may be placed along an interior surface of imaging hood 12 to provide imaging of the open area such that the imaging element 64 is off-axis relative to a longitudinal axis of the hood 12. The off-axis position of element 64 may provide for direct visualization and uninhibited access by instruments from the catheter to the underlying tissue during treatment.

Figure 5:
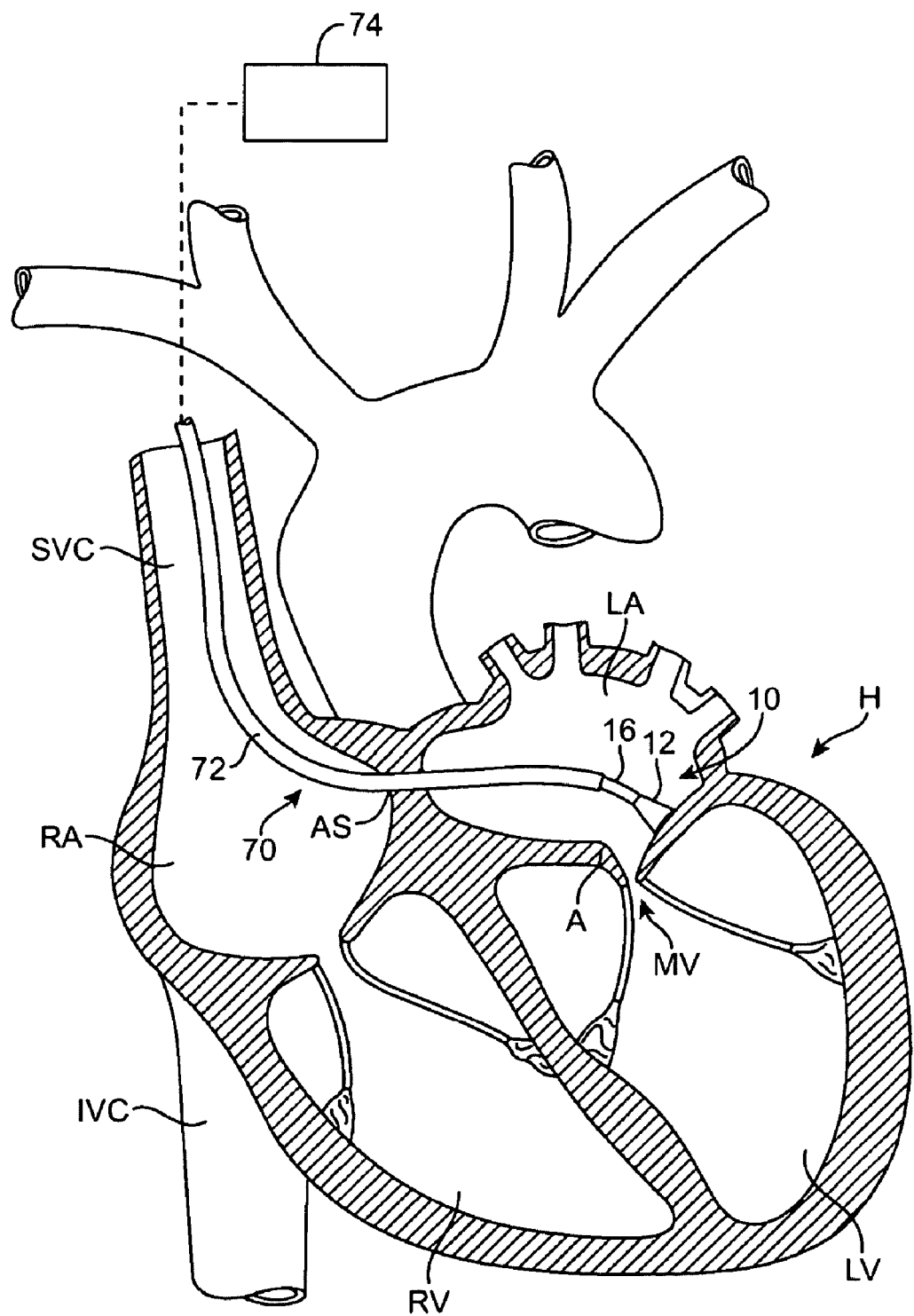
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
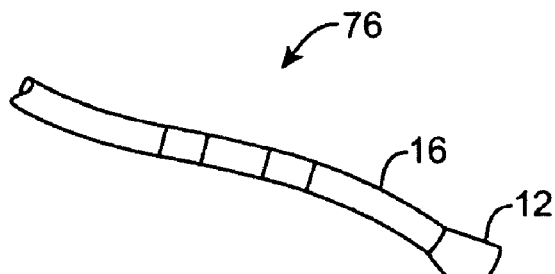
FIGS. 6A to 6C illustrate deployment catheters having one or more optional inflatable balloons or anchors for stabilizing the device during a procedure.
Figure 6B:
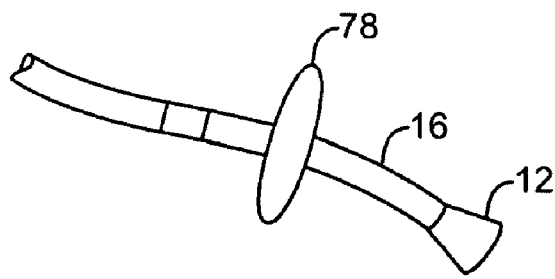
Figure 6C:
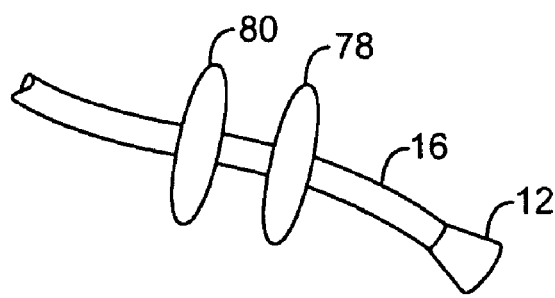

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
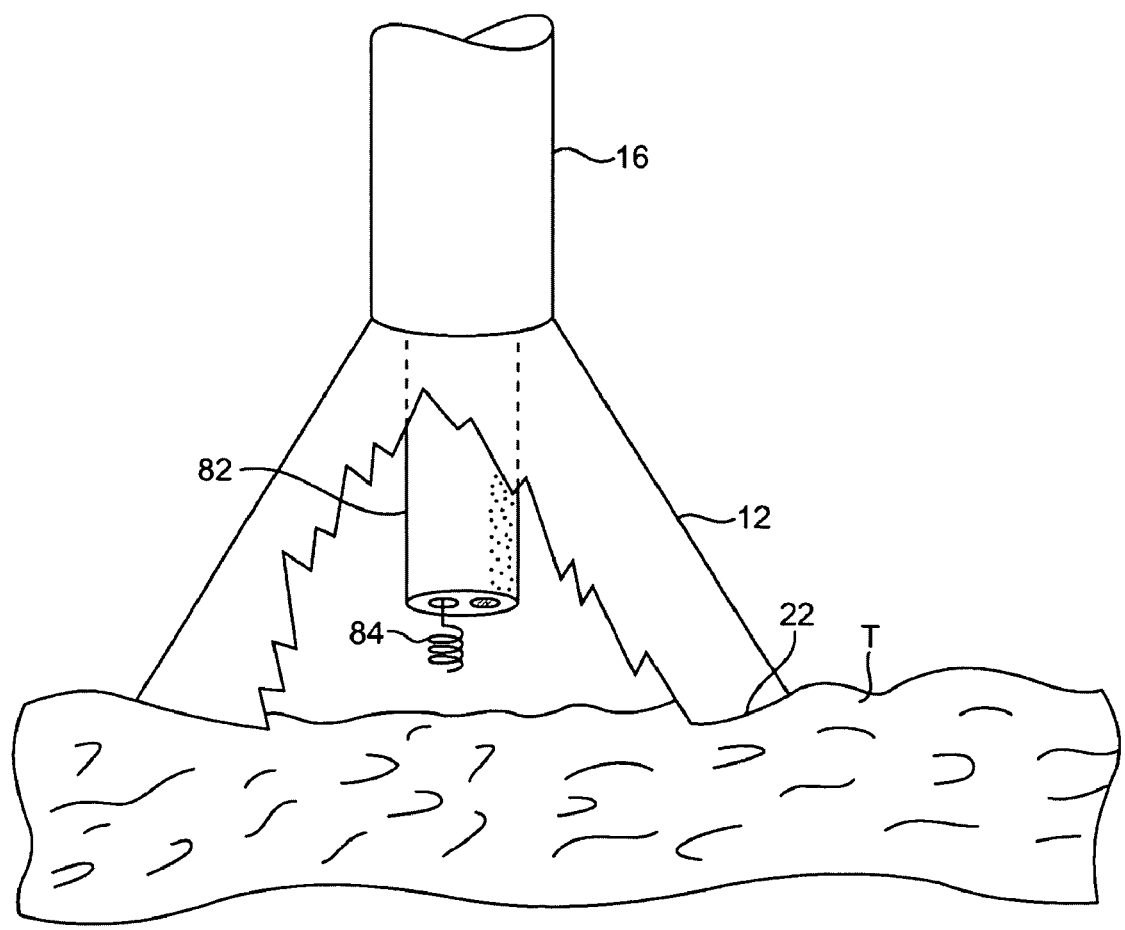
FIGS. 7A and 7B illustrate a variation of an anchoring mechanism such as a helical tissue piercing device for temporarily stabilizing the imaging hood relative to a tissue surface.

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool delivery catheter 82, as shown in FIG. 7A, and into imaging hood 12.

Figure 7B:
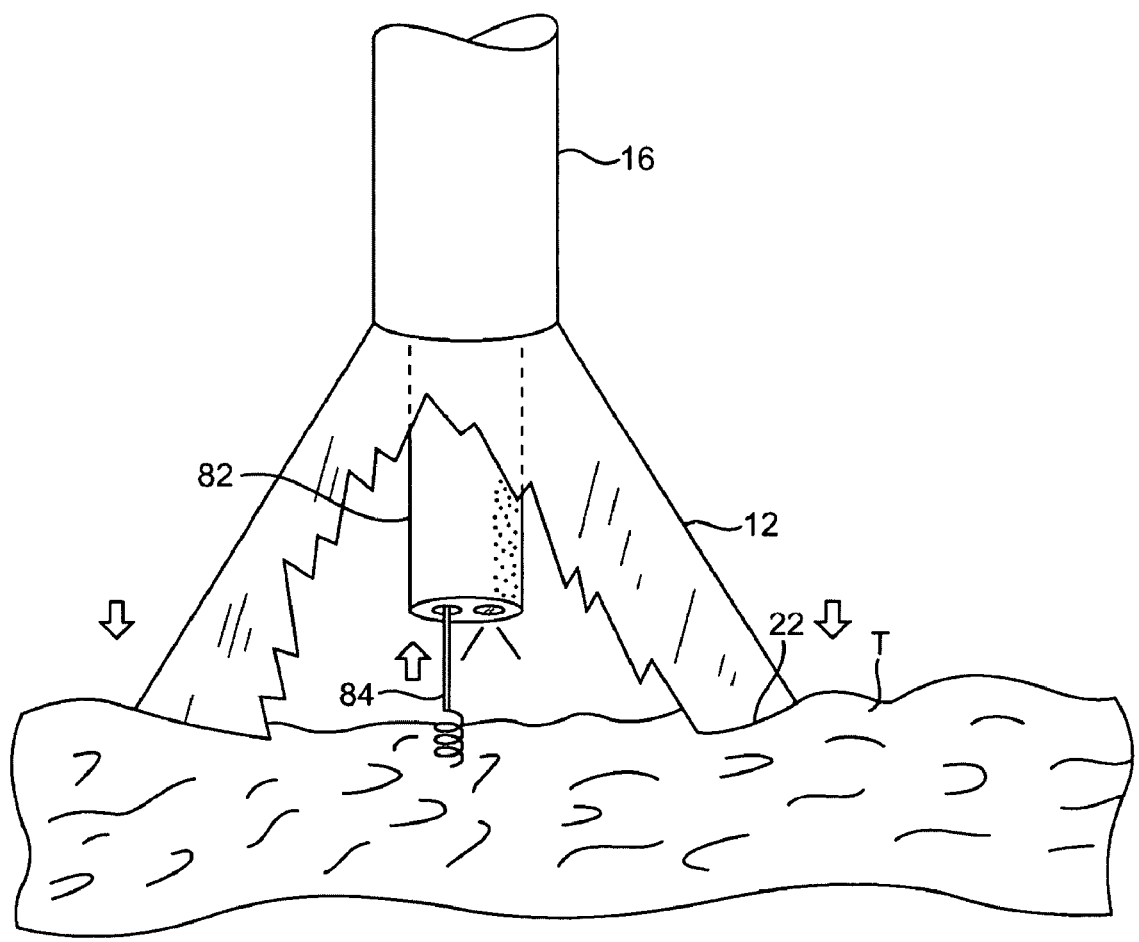

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
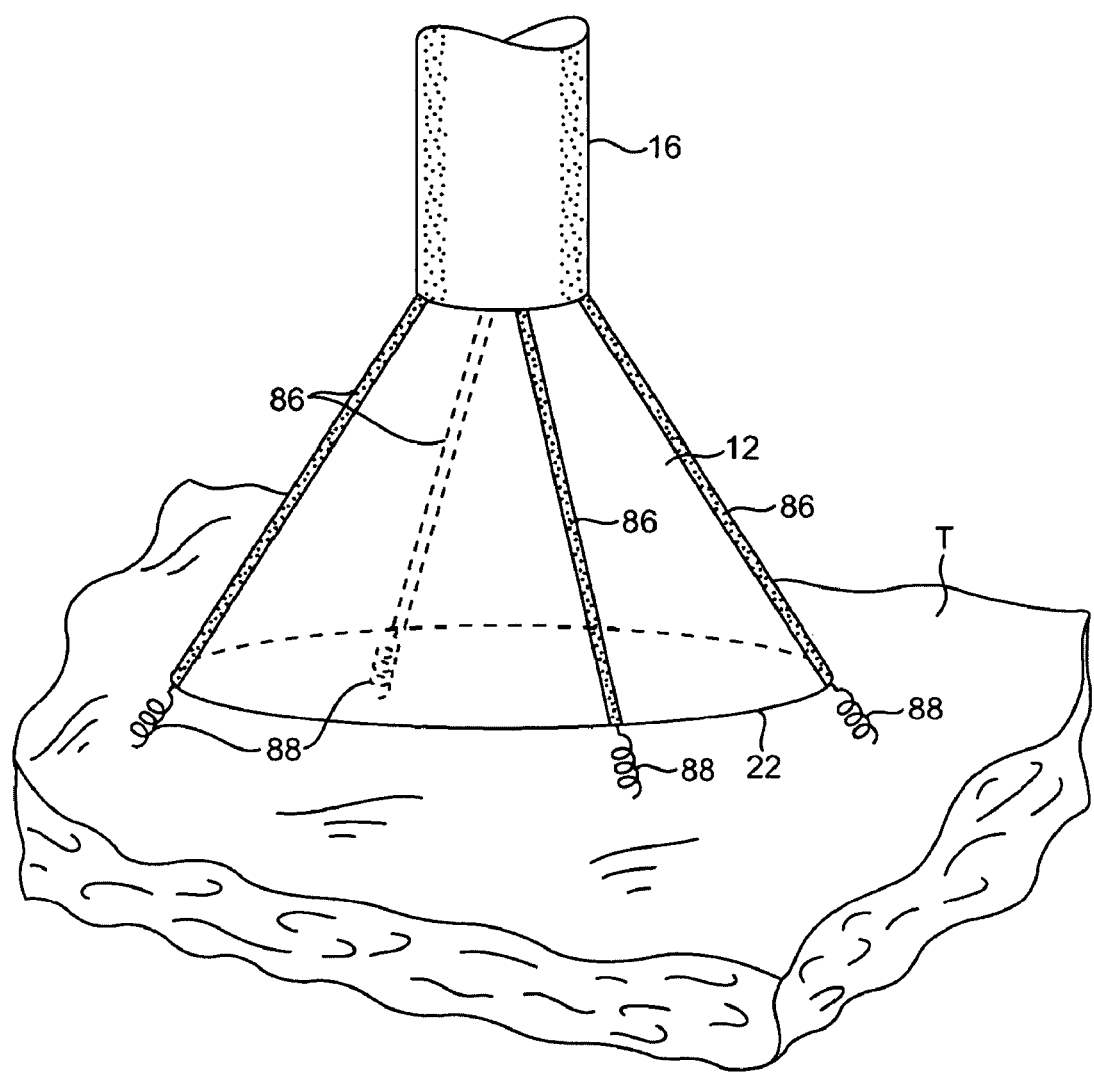
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
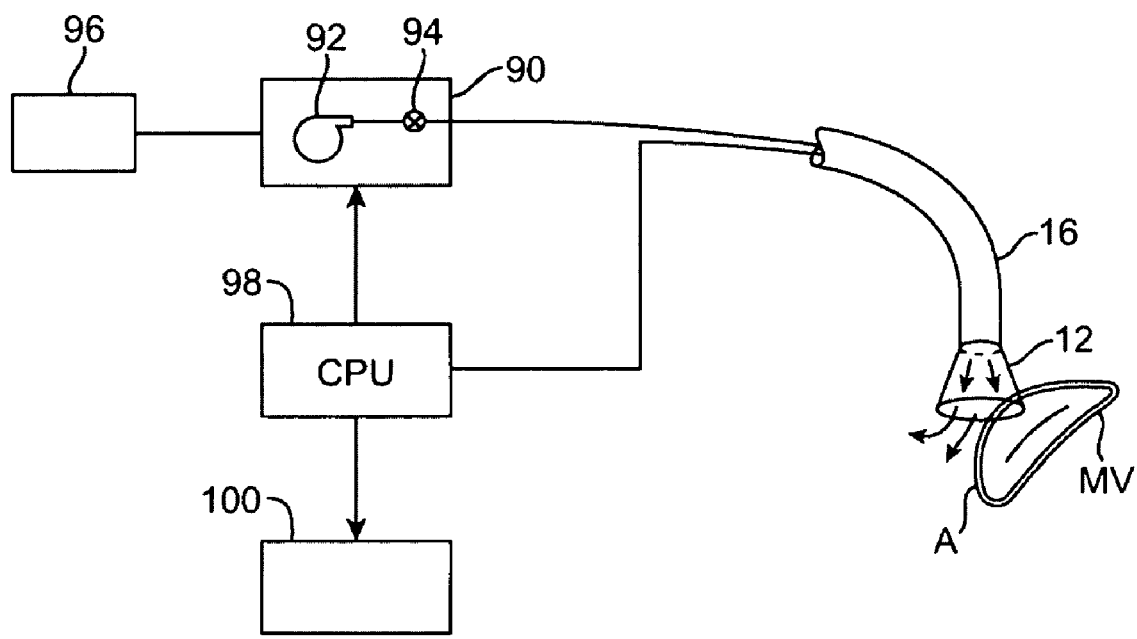
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
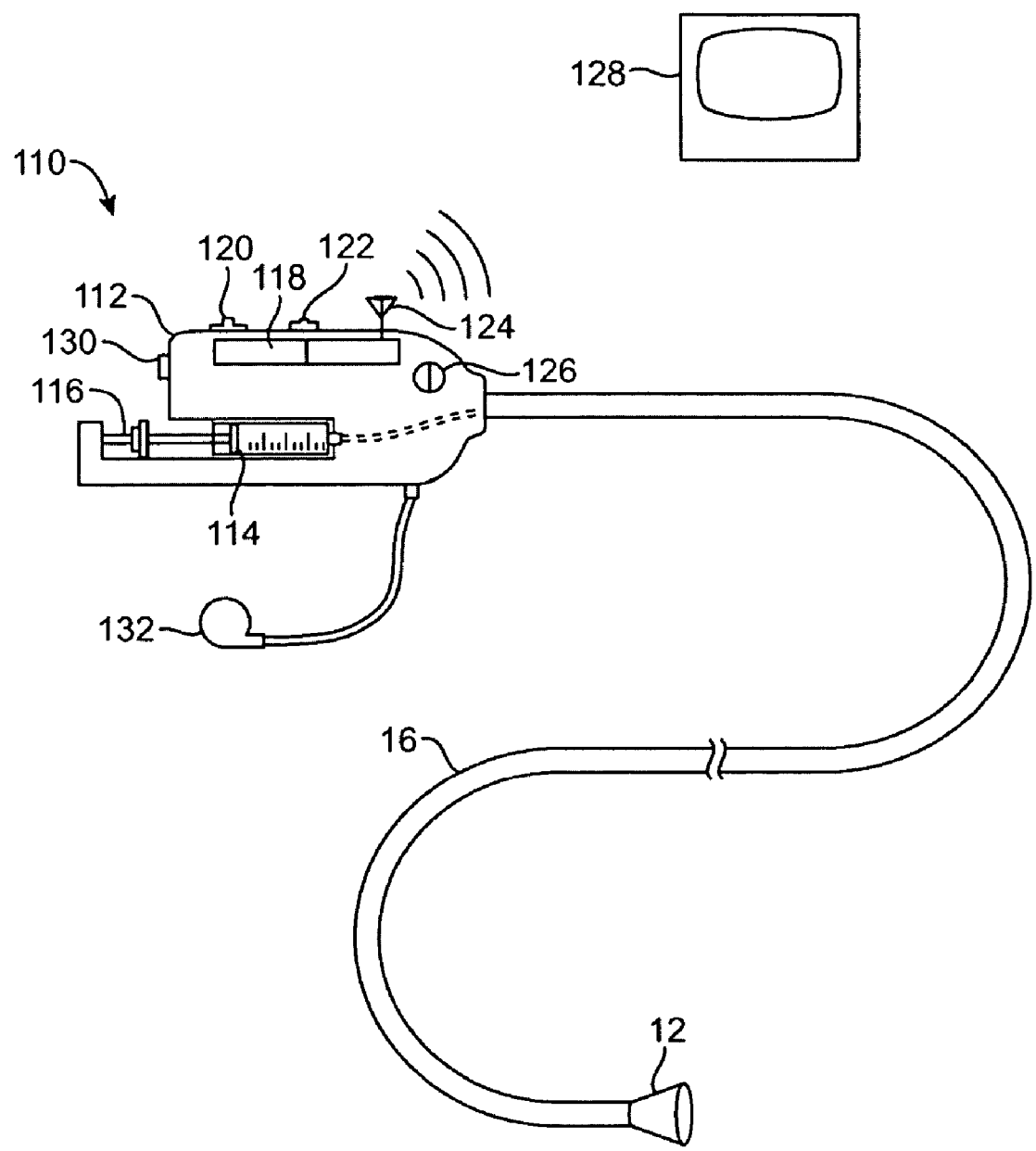
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG. Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
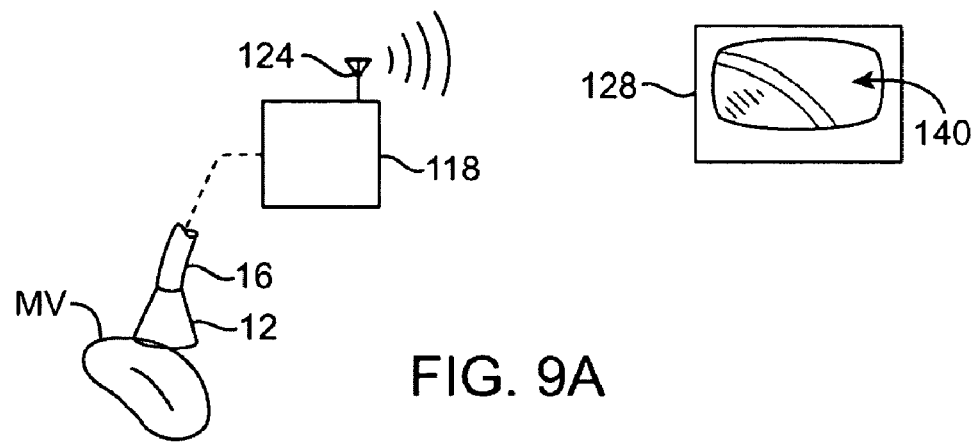
FIGS. 9A to 9C illustrate an example of capturing several images of the tissue at multiple regions.
Figure 9B:
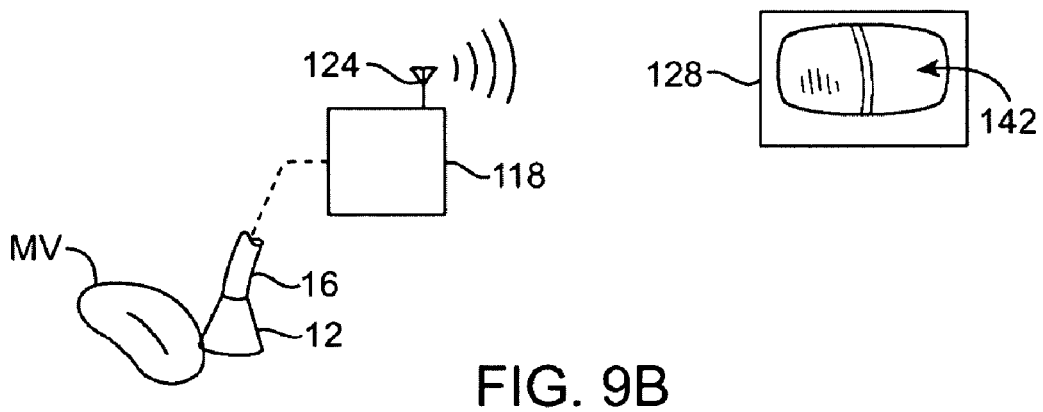
Figure 9C:
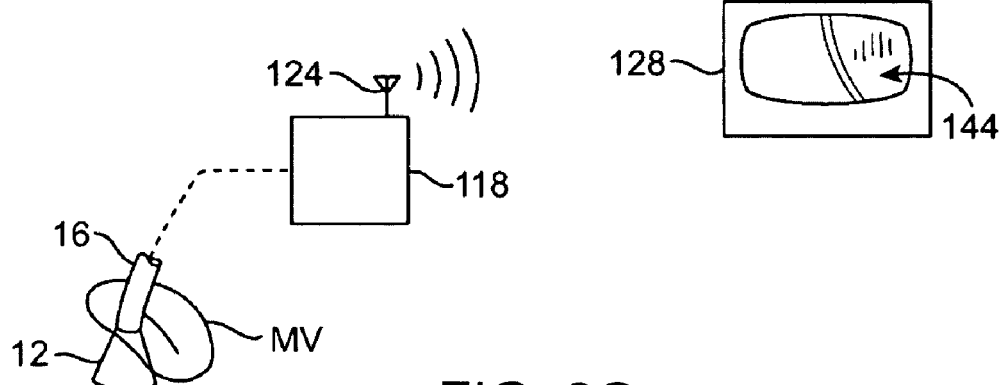

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
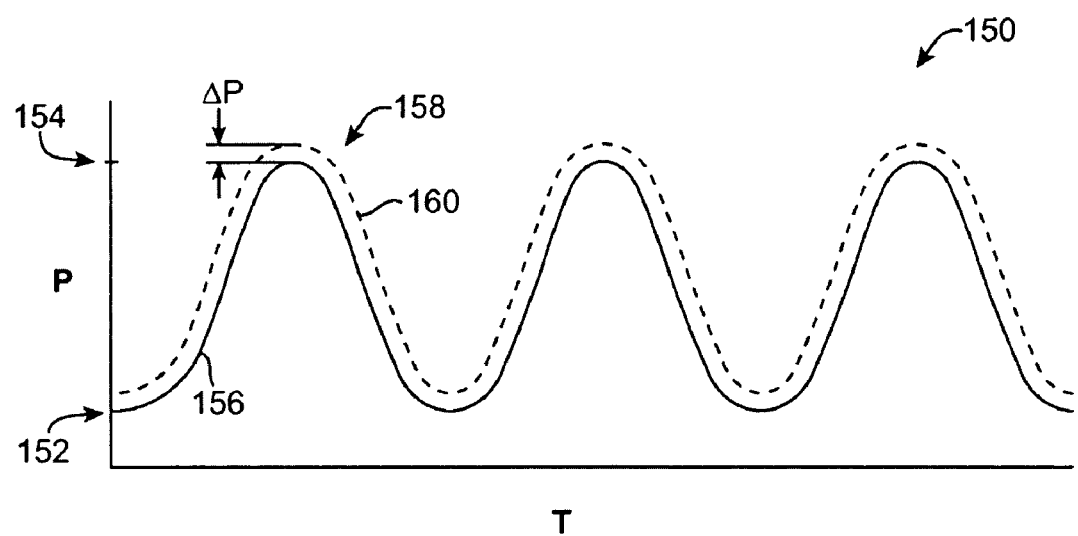
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase $\Delta P$, as illustrated by the pressure difference at the peak systolic pressure 158. This pressure difference, $\Delta P$, may be maintained within imaging hood 12 over the pressure variance of the surrounding blood pressure to maintain a positive imaging fluid pressure within imaging hood 12 to maintain a clear view of the underlying tissue. One benefit of maintaining a constant $\Delta P$ is a constant flow and maintenance of a clear field.

Figure 10B:
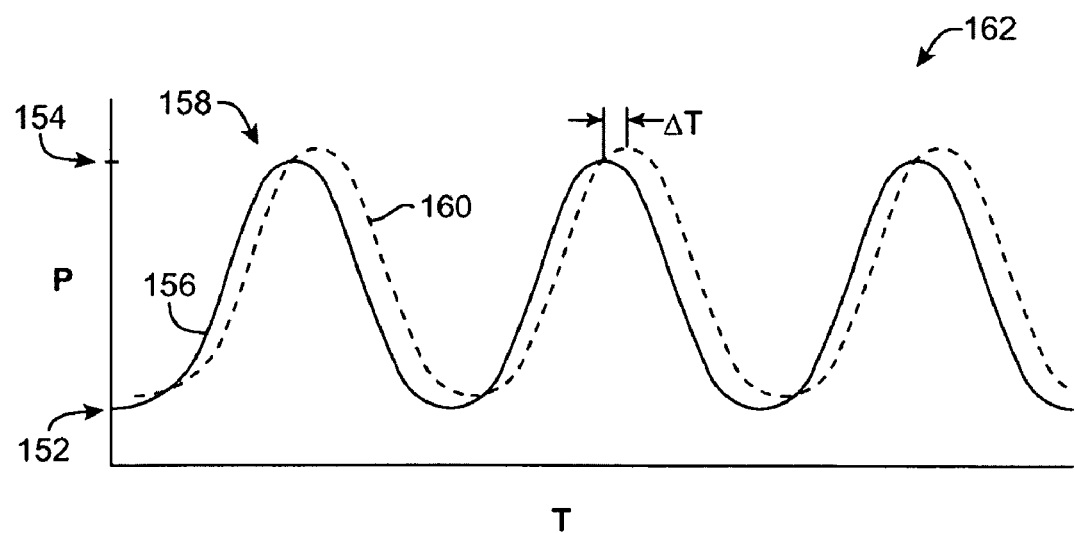

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, $\Delta T$, as illustrated by the shifted fluid pressure 160 relative to the cycling blood pressure 156, although the time delays $\Delta T$ may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

In further controlling the flow of the purging fluid within the hood 12, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood 12 may be maintained for relatively longer periods of time by inhibiting, delaying, or preventing the infusion of surrounding blood into the viewing field.

As shown in the perspective and end views of FIGS. 11A and 11B, respectively, one variation for controlling the flow of the purging fluid within and from hood 12 may include a distensible and/or inflatable membrane 170 which extends over the distal opening of hood 12 to at least partially enclose open area or field 26. A variably-sized aperture 172 may be defined over membrane 170 such that aperture 172 is relatively in-line with deployment catheter 16 such that instruments may be passed directly through aperture 172. Alternatively, aperture 172 may be positioned at other regions over membrane 170, if so desired.

Membrane 170 may be comprised of the same or similar material as the rest of hood 12 or some other elastomeric material which is relatively transparent to allow for viewing through membrane 170 of underlying tissue to be imaged. Moreover, membrane 170 may be comprised of a dual-layer to trap a transparent fluid or gas which may be infused between the layers such that aperture 172 may be forced to contract or reduce in diameter, as shown in FIG. 11B, as indicated by the direction of aperture restriction 174. Imager 176, e.g., CCD, CMOS, etc., is shown in an off-axis position along hood 12 relative to a longitudinal axis of the deployment catheter 16 for imaging the visualized tissue within hood 12. To enlarge aperture 172, the fluid or gas within membrane 170 may be deflated or depressurized such that aperture 172 is enlarged, as indicated by the direction of aperture expansion 178 in the perspective and end views of FIGS. 12A and 12B, respectively. In this manner, the size of aperture 172 may be controllable in real time to range anywhere from completely closing upon itself to seal the interior of hood 12 from the surrounding environment to opening completely to the circumference of hood 12 depending upon the size of aperture 172 to be implemented. Moreover, although aperture 172 is illustrated to be circular, other shapes may be implemented as well, e.g., elliptical, triangular, rectangular, etc., as so desired.

In use, with membrane 170 of hood 12 positioned against a tissue region of interest such as within the heart of the patient, saline or other transparent fluids may be infused within hood 12 such that the hood interior is cleared of any blood or other opaque bodily fluids. The purged blood and fluids may exit from aperture 172 and into the surrounding environment such that a clear field of view remains for imaging through the interior of hood 12 and/or through membrane 170 upon the underlying tissue. Membrane 170 may be infused with the gas or fluid to reduce the diameter of aperture 172. In this manner, aperture 172 may be simply reduced in size. e.g., 1 to 4 mm in diameter, to restrict or reduce the escape of the purging fluid from hood 12 while also restricting or reducing the in-flow of blood back into hood 12 or aperture 172 may be completely sealed shut to retain the purging fluid within. Because membrane 170 is fabricated from a clear or transparent material and the infused gas or fluid is also clear, visualization of the tissue through the membrane 170 may be accomplished unobstructed. Aperture 172 may also be expanded to various diameters to allow for the passage of any number of instruments from catheter 16 for use upon the underlying tissue in any number of procedures.

Figures 13A, 13B:
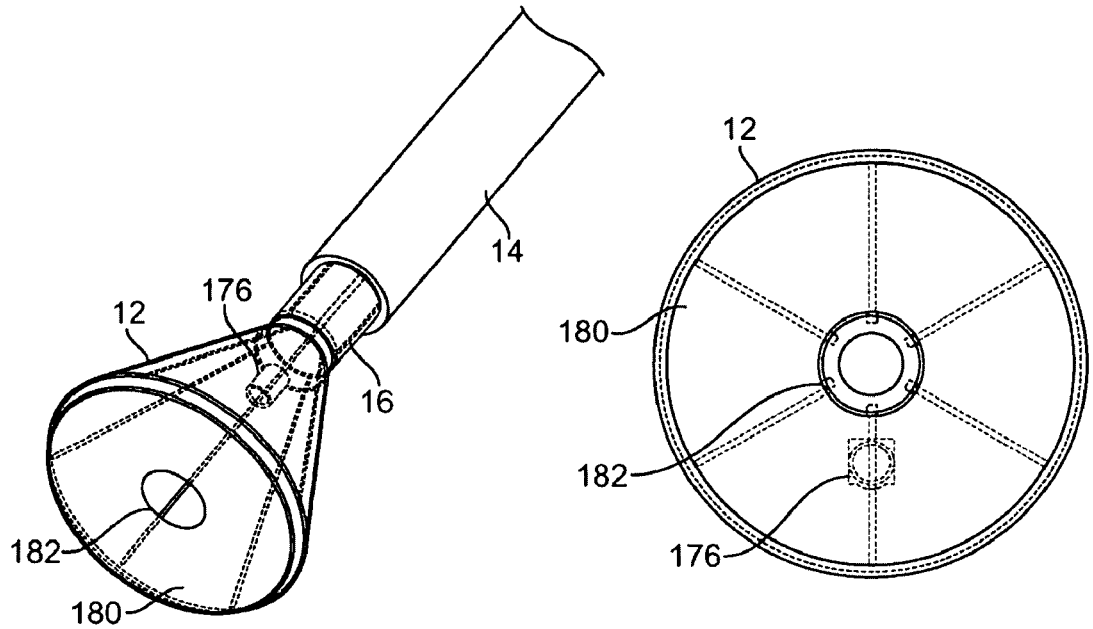
FIGS. 13A and 13B show perspective and end views, respectively, of yet another variation where a flow reduction aperture defined along the hood may be constructed by a distensible membrane.
Figures 14A, 14B:
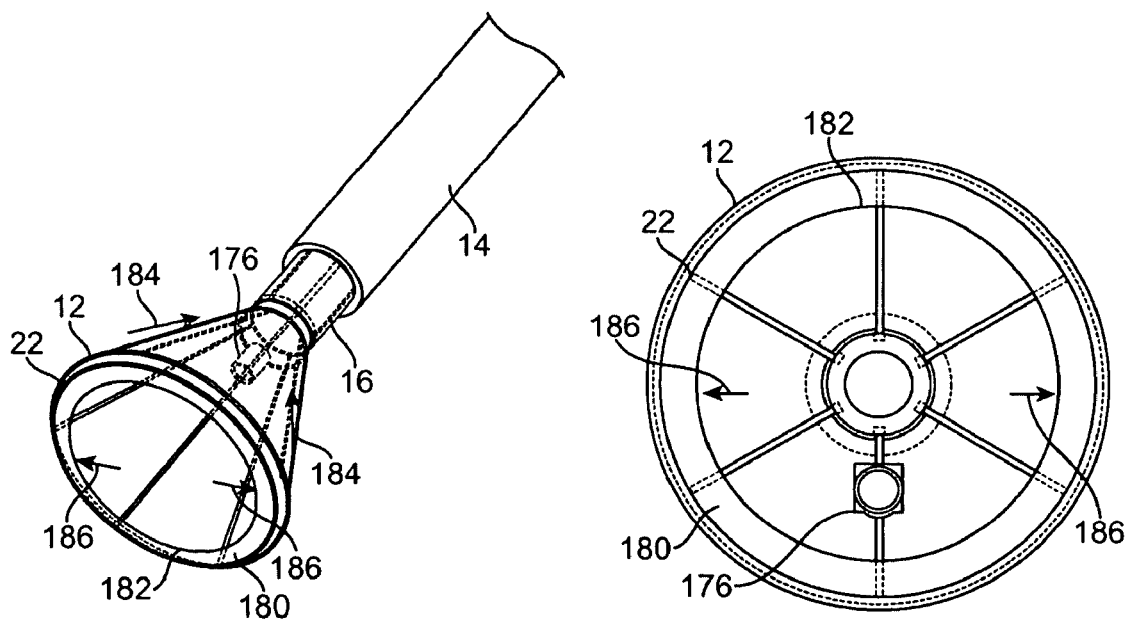
FIGS. 14A and 14B show perspective and end views, respectively, of variation from of FIG. 13A where the membrane may be pulled proximally relative to the catheter to expand the aperture diameter.

FIGS. 13A and 13B illustrate another variation of a flow reduction aperture that is variable in size in the perspective and end views, respectively. In this variation, a transparent distensible membrane 180 may be positioned or stretched over a scaffold or frame to form hood 12. Membrane 180 may further extend over atraumatic contact lip or edge 22 to form a covering over the distal opening of hood 12. Aperture 182 may be defined along membrane 180 to form an aperture, e.g., 1 to 4 mm in diameter, for use in visualizing tissue regions. The size of aperture 182 may be varied, e.g., by pulling membrane 180 proximally, as indicated by the direction of membrane withdrawal 184 in the perspective view of FIG. 14A, relative to hood 12 via a retraction mechanism such as pull wires or tensioning members embedded in the catheter. As the membrane is distensible, retraction 184 of membrane 180 may expand aperture 182, as indicated by the direction of aperture expansion 186 in the end view of FIG. 14B to allow for the passage of any number of instruments into and/or through hood 12. Because of the distensible nature of membrane 180, release of the membrane may allow aperture 182 to naturally retract into a smaller opening. Aperture 182 may be sized in use at any time during a procedure, as described above.

Figure 15A:
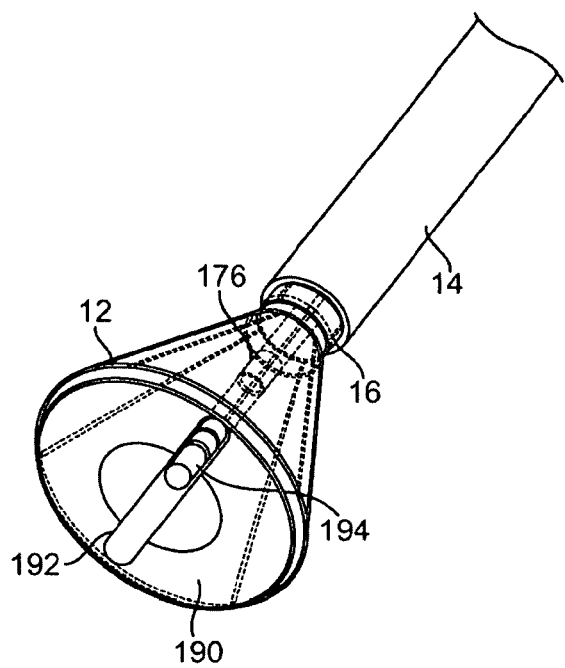
FIGS. 15A and 15B show perspective and end views, respectively, of another variation where the flow reduction aperture is defined along the distal end of the hood in a transverse orientation relative to the catheter longitudinal axis.
Figure 15B:
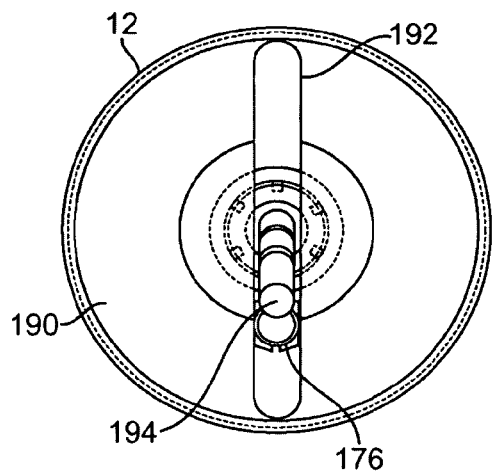

Aside from variably sized apertures, openings having other configurations may be utilized to control, restrict, or inhibit the flow of fluids from or through the hood. An example is illustrated in the perspective and end views of FIGS. 15A and 15B, respectively, which shows hood 12 having a transparent covering or membrane 190, as above, but defining an aperture 192 which is slotted transversely relative to catheter 16. Slotted aperture 192 may extend along the entire length of the diameter of membrane 190 or just along a portion thereof to facilitate access of an instrument 194, e.g., ablation instrument, to the underlying visualized tissue. Moreover, aperture 192 may also function, e.g., as a template for ablation probes to create linear ablation lesions on the contacted tissue by following the slotted aperture 192 as well as restricting or inhibiting the flow of the purging fluid from hood 12.

Figure 16A:
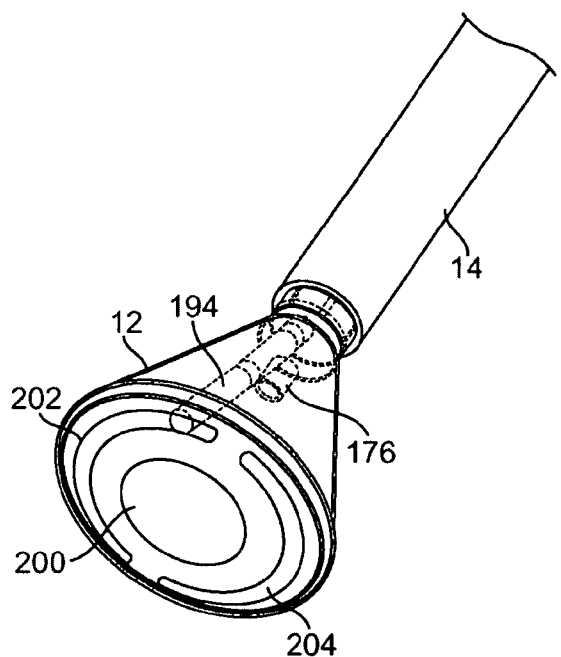
FIGS. 16A and 16B show perspective and end views, respectively, of another variation where the flow reduction aperture is defined along the distal end of the hood in one or more curved patterns.
Figure 16B:
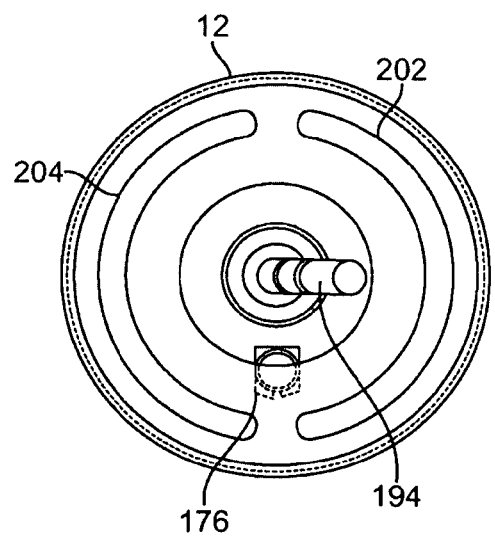

Another variation of an aperture which is configured into a shape is illustrated in the perspective and end views of FIGS. 16A and 16B, respectively. In this particular variation, one or more slotted openings may form curved apertures 202, 204 which extend in an arcuate or curved manner over covering or membrane 200. Although two symmetric apertures 202, 204 are illustrated, a single curved aperture may be utilized or several curved apertures which extend circumferentially in uniform or non-uniform discrete sections may also be utilized. As above, these curved apertures 202, 204 may be utilized as a template for the creation of curved lesions upon the underlying tissue while also restricting or inhibiting the flow of the purging fluid from hood 12. Moreover, this or any of the other variations may be constructed either with an inflatable double-layered distensible membrane or with a single-layered membrane.

Figure 17A:
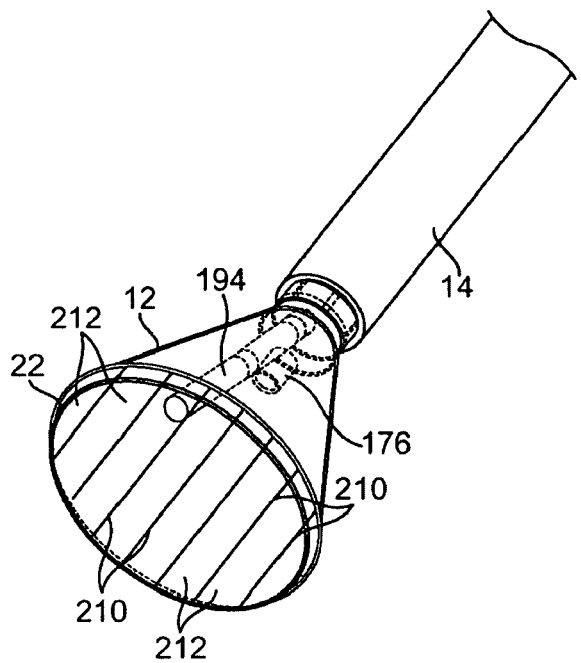
FIGS. 17A and 17B show perspective and end views, respectively, of another variation having one or more lengths of an expandable or distensible material defined over the distal opening.
Figure 17B:
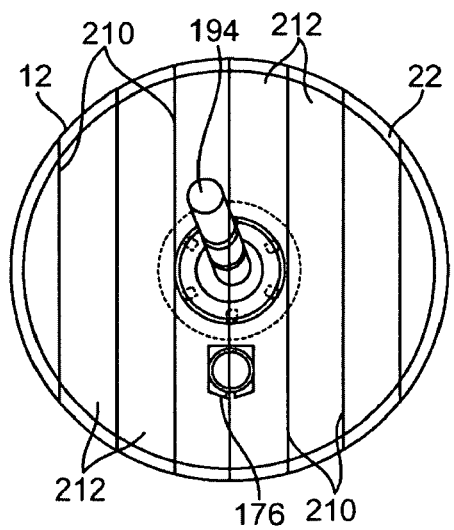
Figure 18A:
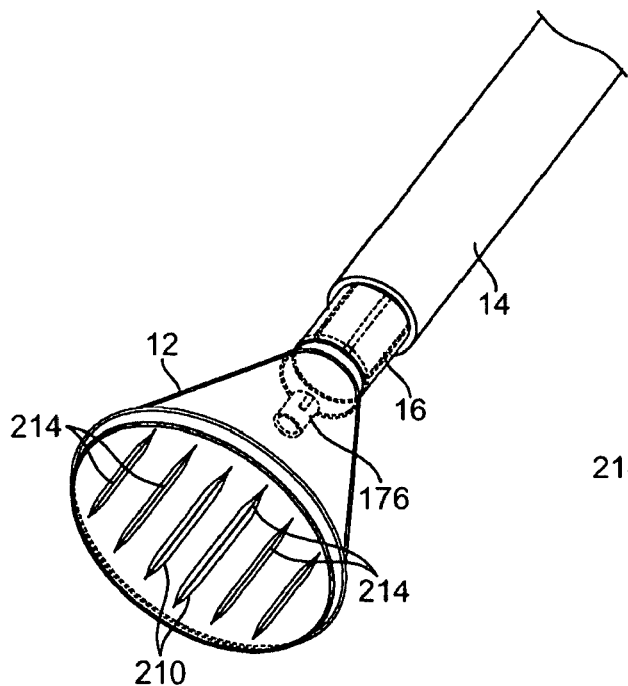
FIGS. 18A and 18B show perspective and end views, respectively, of the variation of FIG. 17A where the one or more lengths of expandable or distensible material may be inflated or expanded over the opening of the hood to reduce or restrict flow to or from the hood.
Figure 18B:
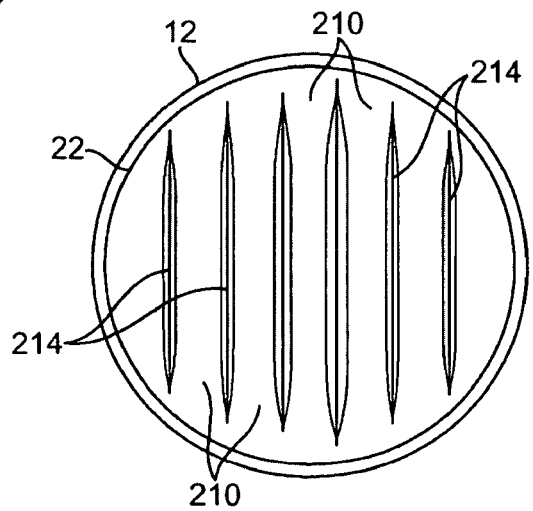

In yet another variation, FIGS. 17A and 17B illustrate perspective and end views, respectively, of a hood 12 which may utilize a plurality of inflatable elongate strips or barriers 210 which extend over the opening of hood 12 adjacent to one another such that the entire distal opening of hood 12 may be closed by inflation or expansion of these strips or barriers 210. These strips or barriers may be comprised of a transparent elastomeric material such as silicon, polyurethane, latex, etc. each having a width ranging from, e.g., 2 to 3 mm, and which are each attached at opposing ends of hood 12. In their non-inflated state, strips or barriers 210 may form a number of openings 212 between each strip through which an instrument 194 may be passed through. Once hood 12 has been purged of blood, each strip or barrier 210 may be inflated at least partially to close the openings 212 and to restrict the flow of purging fluid from hood 12 and the flow of blood back into hood 12. Alternatively, strips or barriers 210 may be fully inflated or expanded such that each strip or barrier 210 forms an overlapping portion 214 with an adjacent strip or barrier 210 to fully prevent or inhibit fluid exchange between the hood interior and the surrounding bodily fluids while maintaining visualization of the underlying tissue through the inflated or elongated strips or barriers 210, as shown in the perspective and end views of FIGS. 18A and 18B, respectively. Moreover, the strips or barriers 210 and hood 12 can share the same fluid or gas lining to simultaneously perform inflation or deflation operations during the purging process.

The purging fluid can be irrigated out of hood 12 when additional purging fluid is injected, consequently increasing fluid pressure within hood 12 to force the fluid through the overlapping gaps 214 of the strips or barriers 210. As described above, any number of therapeutic instruments 194 (e.g., ablation probes, guidewires, needles, graspers, dilators, etc.) can be deployed out of hood 12 through openings 212. In addition, instruments 194 are able to navigate linearly along and through these openings 212 to facilitate operations such as the formation of linear tissue lesions for atrial or ventricular fibrillation, etc.

Figures 19A, 19B:
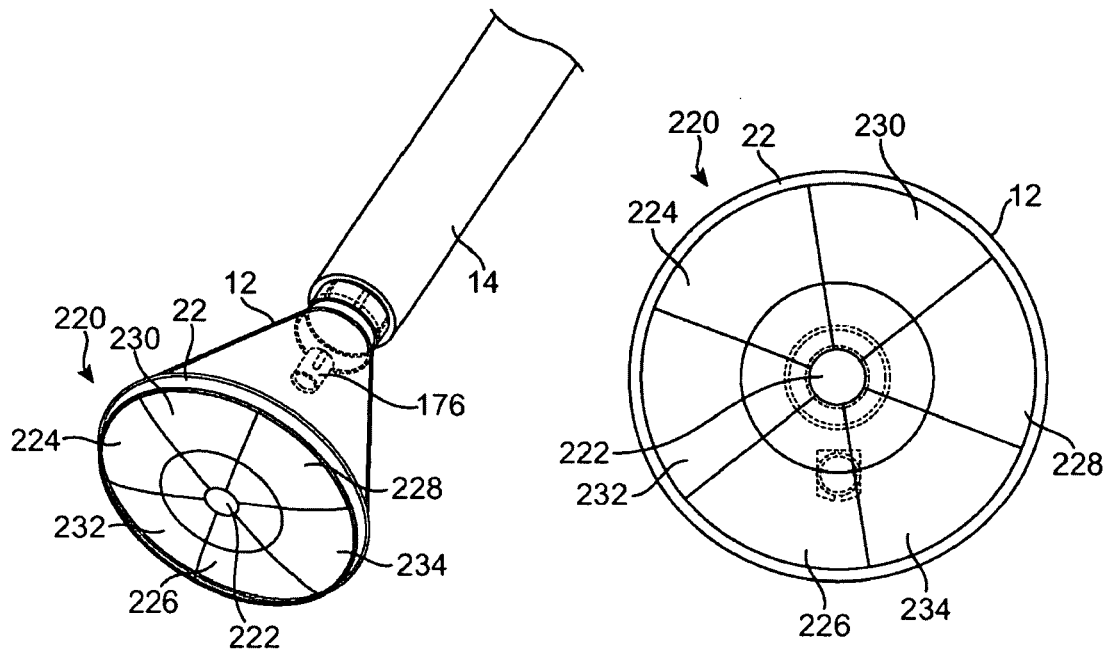
FIGS. 19A and 19B show perspective and end views, respectively, of another variation having one or more slotted openings which are rotatable relative to the catheter to alter the size of the openings of the one or more slots.

In yet another variation, FIGS. 19A and 19B illustrate perspective and end views, respectively, of hood 12 which comprises a rotatable barrier 220 which may pivot or rotate relative to one or more stationary segments 230, 232, 234 which are non-moving relative to hood 12 to transition between an open and closed configuration. Rotatable barrier 220 may be formed by one or more rotatable segments 224, 226, 228 which are spaced, uniformly or non-uniformly, apart from one another and each joined at a common pivot or rotational point 222 located near or at the center of hood 12. The stationary segments 230, 232, 234 may also be spaced from one another in a complementary manner relative to rotatable segments 224, 226, 228 and each may be connected to hood 12 around the periphery of lip or edge 22 such that when each of the segments of both the rotatable barrier 220 and the stationary segments are aligned adjacent to one another, the interior of hood 12 may be sealed to retain the purging fluid within.

Figures 20A, 20B:
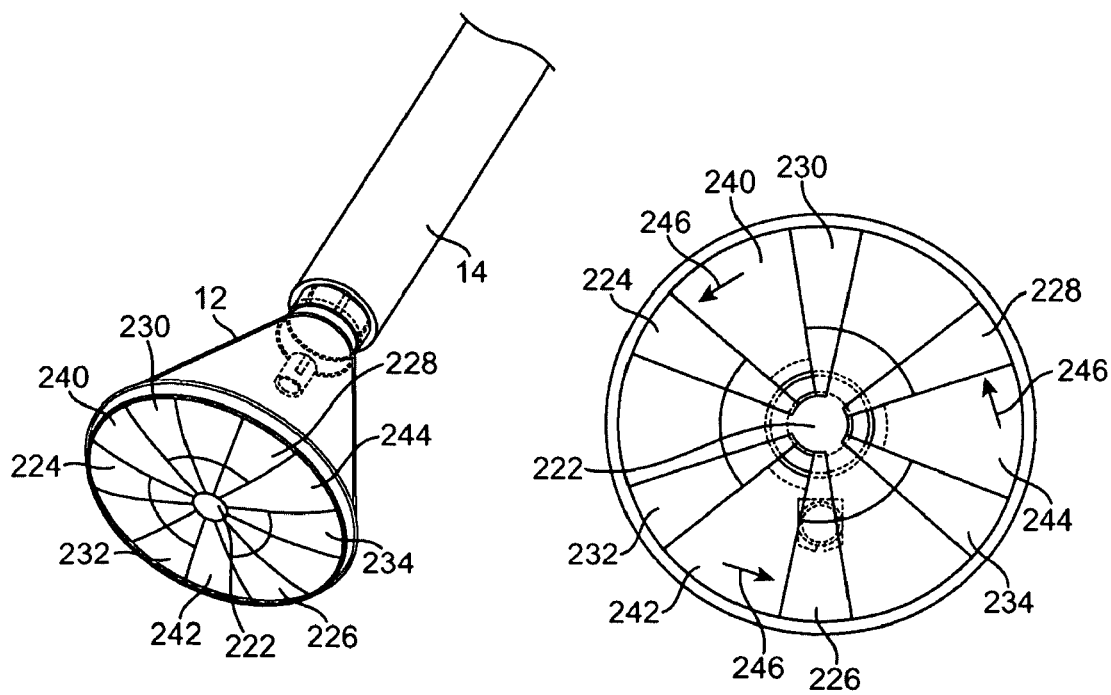
FIGS. 20A and 20B show perspective and end views, respectively, of the variation of FIG. 19A where the one or more slotted openings may be rotated relative to the catheter into an open configuration.

By rotating the barrier 220 about pivot 222, e.g., counter-clockwise as indicated by the direction of rotation 246 or clockwise relative to stationary segments 230, 232, 234 and the longitudinal axis of hood 12, segmented openings 240, 242, 244 may be formed between each respective adjacent segment, as shown in the perspective and end views of FIGS. 20A and 20B. By fully rotating barrier 220, segmented openings 240, 242, 244 may be fully opened, as shown in the perspective view of FIG. 21. The size of the segmented openings 240, 242, 244 formed can thus be controlled by rotating barrier 220 accordingly. Irrigation and/or deployment of instruments through hood 12 can be made through these formed segmented openings 240, 242, 244. Hood 12 can be used for visualization and therapeutic procedures with barrier 220 in either its fully closed or fully opened configuration or any size opening formed.

Another variation is illustrated in the perspective and end views of FIGS. 22A and 22B, respectively, where hood 12 may include a mesh frame 250 fabricated from a transparent polymeric material such as PVC, polyurethane, PET, etc. which covers the opening of hood 12 to restrict or reduce the flow of fluid from and into hood 12. The plurality of distributed openings 252 across mesh frame 250 may allow for the purging fluid to be evenly irrigated out of hood 12 as compared to a single relatively larger aperture. Any number of therapeutic instruments as described above can be deployed by passing them through the openings 252 in the mesh frame 250. Moreover, the size of openings 252 may be varied depending upon the size of the instruments to be used as well as the desired overall area to be imaged.

FIGS. 23A to 23D illustrate perspective views of yet another variation of a hood assembly covered by a membrane 260 and which defines an aperture 262 having a diameter of, e.g., 1 to 4 mm, over membrane 260 at a distal end of hood 12. This variation in particular shows an example of an assembly which is configured to restrict or control fluid flow into and out of hood 12 and which is also collapsible into a low-profile configuration which is utilizable as a tissue dilator.

Figures 23A, 23B:
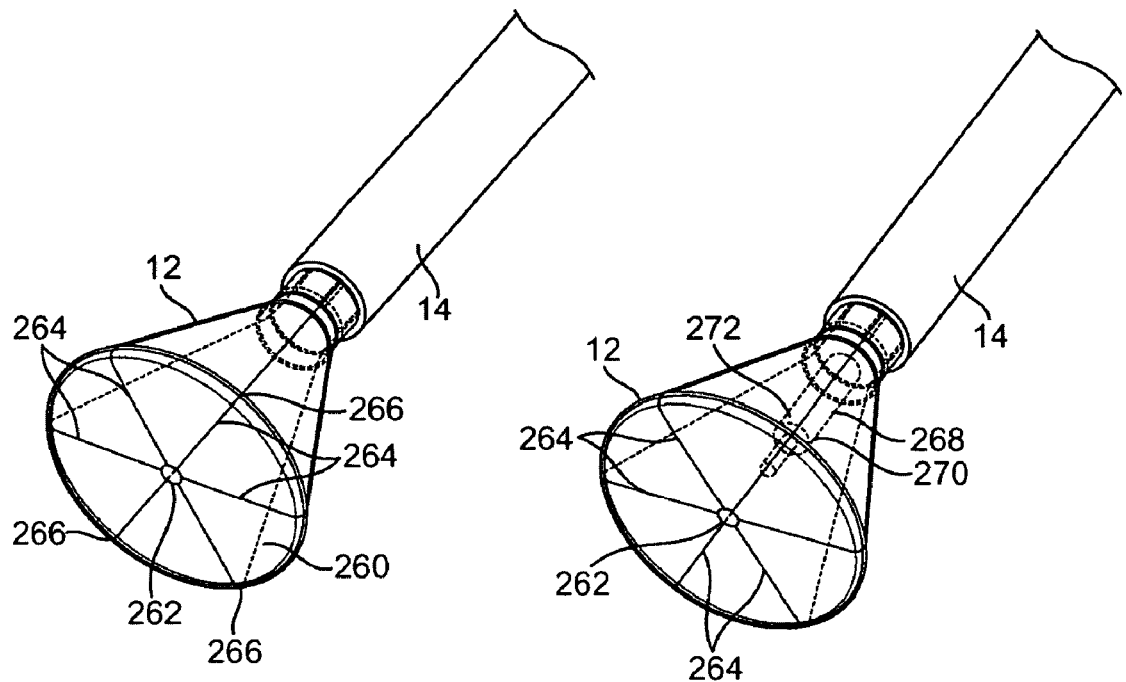
FIGS. 23A to 23D show perspective views of another variation where a hood may be reduced into its low-profile configuration by advancing an instrument such as a dilator distally into the hood and into engagement with the flow reduction aperture to collapse the hood.

As shown, hood 12 may be defined by several support struts 264 made from materials such as Nitinol, nylon, Mylar, etc., which extend from the proximal end of hood 12 and define curved or bent portions 266 which terminate at the distal end of hood 12 at the flow control aperture 262. A strut may also form a ring surrounding aperture 262 to provide circumferential strength to aperture 262, as shown in FIG. 23A. In its deployed configuration, hood 12 with aperture 262 may be utilized to visualize and/or treat tissue while restricting or controlling the flow of fluid from and into hood 12 via aperture 262. To deploy and/or collapse hood 12 between its deployed and low-profile configurations, an instrument 268 such as a dilator having an atraumatic tip 270 projecting distally from a shoulder 272 may be advanced distally through the deployment catheter and into hood 12, as shown in FIG. 23B.

Figures 23C, 23D:
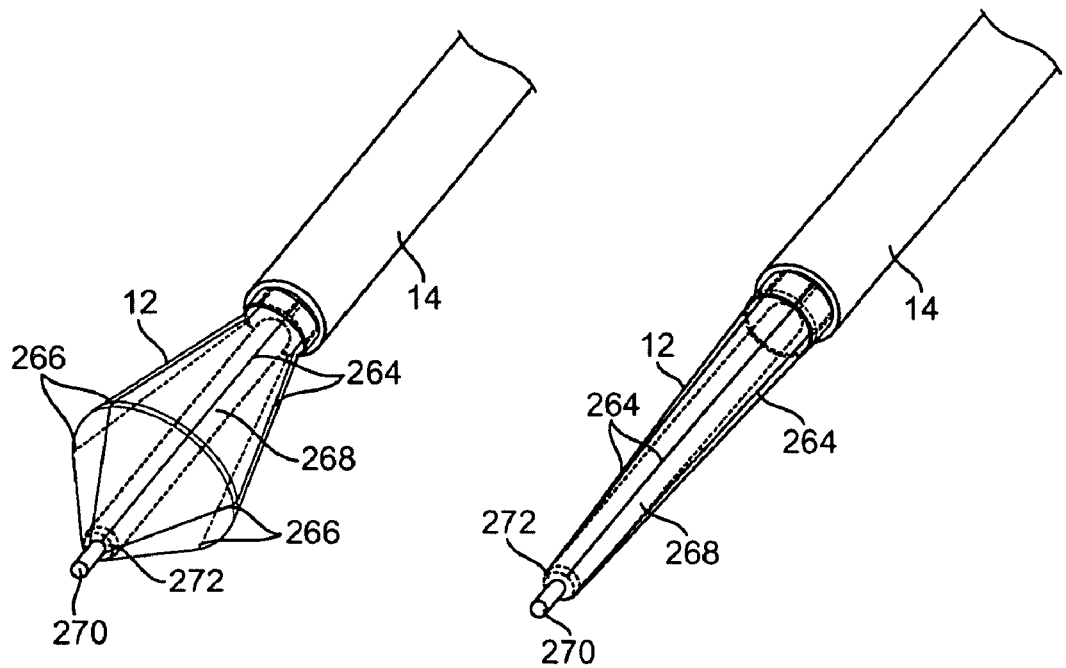
Figure 24A:
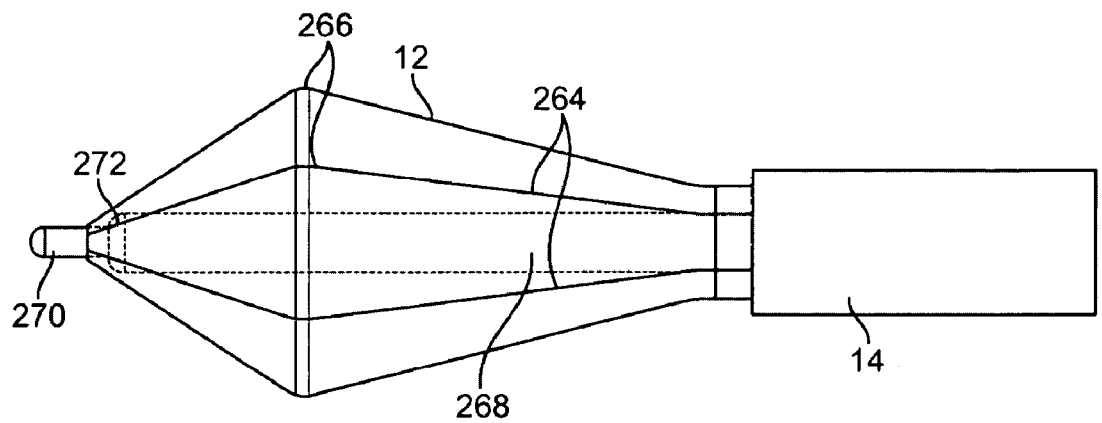
FIGS. 24A and 24B show side views of the device of FIG. 23A illustrating engagement of the instrument within the aperture and the collapse of the hood upon further distal advancement of the instrument.
Figure 24B:
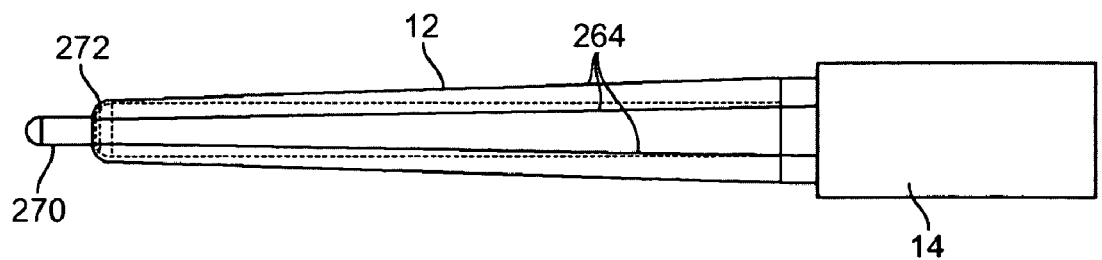

Instrument 268 may be further advanced until tip 270 projects through aperture 262 and shoulder 272 engages or abuts against the interior of membrane 260 surrounding aperture 262. As instrument 268 is pushed further distally, the curved or bent portions 266 of support struts 264 may become start to become straightened relative to instrument 268 and support struts 264 may begin to collapse, as shown in FIG. 23C. Once instrument 268 has been fully advanced into its distal position, portions 266 and support struts 264 may be fully collapsed against instrument 268 into a low-profile configuration, as shown in FIG. 23D. FIGS. 24A and 24B illustrate side views of support struts 264 collapsing and portions 266 extending into their straightened configurations against instrument 268.

With this variation, hood 12 may be collapsed for delivery without having to retract hood 12 into a catheter sheath 14. Additionally, with the ability to collapse hood 12 distally rather than proximally, projecting tip 270 may be used to actively dilate tissue openings, cavities, flaps, etc. such as the fossa ovalis or the coronary sinus. With direct dilation, hood 12 may be guided to pass through the tissue opening, cavity, or flap in a single process. Procedures such as transseptal access or coronary sinus cannulation can therefore be performed more efficiently.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. An apparatus configured to control fluid flow, comprising:
   a barrier projecting distally from a deployment catheter and defining an open area therein, wherein the open area is in fluid communication with at least one lumen defined through the catheter;
   at least one membrane extending over a distal opening defined by the barrier such that the membrane partially covers the open area and further defines at least one aperture through the membrane, wherein the aperture is sized to control a flow of a clearing fluid through the aperture and to an environment external to the barrier, the fluid being infused within the open area via the at least one lumen; and
   an imaging element positioned to image the open area through the clearing fluid.

2. The apparatus of claim 1 wherein the membrane comprises an inflatable dual-membrane.

3. The apparatus of claim 1 wherein the aperture is controllable to variably alter its diameter.

4. The apparatus of claim 1 wherein the membrane is distensible such that proximal tensioning or releasing of the barrier correspondingly controls a diameter of the aperture.

5. The apparatus of claim 1 wherein the aperture is slotted transversely relative to the catheter.

6. The apparatus of claim 1 wherein the aperture comprises at least one slotted opening which extends in an arcuate or curved manner over the membrane.

7. The apparatus of claim 1 wherein the at least one membrane comprises a plurality of inflatable strips or barriers extending over the open area such that inflation of the strips or barriers controls a size of a plurality of elongate slots.

8. The apparatus of claim 1 wherein the at least one membrane comprises a plurality of movable segments which are rotatable relative to one or more stationary segments which are non-moving relative to the barrier, wherein rotation of the movable segments transition a plurality of apertures between an open and closed configuration.

9. The apparatus of claim 1 wherein the at least one membrane defines a meshed membrane.

10. The apparatus of claim 1 further comprising a dilator which is translatable relative to the barrier, wherein distal translation of the dilator engages the aperture and transitions the barrier to a low-profile configuration.

11. The apparatus of claim 1 wherein the aperture has a diameter of 1 to 4 mm.

12. The apparatus of claim 1 wherein the imaging element comprises a CCD, CMOS, or optical fiber imager.

13. A method for controlling fluid flow, comprising:
positioning a barrier in an expanded configuration projecting distally from a deployment catheter and defining an open area therein proximate or adjacent to a tissue region of interest, wherein at least one membrane extends over a distal opening defined by the barrier such that the membrane partially covers the open area;
infusing a clearing fluid into the open area while visualizing through the open area such that an opaque fluid is purged at least partially from the open area and to an environment external to the barrier through at least one aperture defined along the membrane; and
inhibiting the flow of the clearing fluid from the open area through the at least one aperture.

14. The method of claim 13 wherein visualizing within the open area comprises imaging the open area via a CCD, CMOS, or optical fiber imager.

15. The method of claim 13 further comprising adjusting a size of the at least one aperture.

16. The method of claim 15 wherein adjusting comprises inflating or deflating the at least one membrane such that the aperture size is correspondingly adjusted.

17. The method of claim 13 further comprising tensioning or releasing the barrier such that a diameter of the at least one aperture is correspondingly sized.

18. The method of claim 13 further comprising rotating a plurality of movable segments relative to a plurality of stationary segments which are non-moving relative to the barrier such that relative rotation transitions a plurality of apertures between an open and closed configuration.

19. The method of claim 13 further comprising advancing a dilator into the open area such that the dilator engages the aperture.

20. The method of claim 19 further advancing the dilator relative to the barrier such that the barrier collapses into a low-profile configuration against the dilator.

21. The method of claim 13 further comprising advancing an instrument into the open area to treat tissue underlying the barrier.

22. The method of claim 13 further comprising ablating the tissue while visualizing through the open area.

23. The method of claim 22 wherein ablating the tissue comprises ablating the tissue defined by the at least one aperture.

24. An apparatus configured to control fluid flow, comprising:
a barrier projecting distally from a deployment catheter and defining an open area therein, wherein the open area is in fluid communication with at least one lumen;
at least one membrane covering the open area and defining at least one aperture which is sized to control a flow of a clearing fluid infused within the open area via the at least one lumen, wherein the at least one membrane comprises a plurality of inflatable strips or barriers extending over the open area such that inflation of the strips or barriers controls a size of a plurality of elongate slots; and
an imaging element positioned to image the open area through the clearing fluid.

25. The apparatus of claim 24 wherein the membrane comprises an inflatable dual-membrane.

26. The apparatus of claim 24 wherein the aperture is controllable to variably alter its size.

27. The apparatus of claim 24 further comprising a dilator which is translatable relative to the barrier, wherein distal translation of the dilator engages the aperture and transitions the barrier to a low-profile configuration.

28. The apparatus of claim 24 wherein the imaging element comprises a CCD, CMOS, or optical fiber imager.

29. An apparatus configured to control fluid flow, comprising:
a non-inflatable fluid barrier projecting distally from a deployment catheter and defining an open area therein;
a membrane extending over a distal opening defined by the barrier such that the membrane partially encloses the open area and further defines at least one aperture along the membrane, wherein the aperture is sized to inhibit a flow of a clearing fluid infused within the open area via at least one lumen defined through the catheter, and wherein the open area is in fluid communication through the aperture with an environment external to the barrier; and
an imaging element positioned to image the open area through the clearing fluid.

30. The apparatus of claim 29 wherein the aperture is controllable to variably alter its diameter.

31. The apparatus of claim 29 wherein the membrane is distensible such that proximal tensioning or releasing of the barrier correspondingly controls a diameter of the aperture.

32. The apparatus of claim 29 wherein the aperture comprises at least one slotted opening which extends in an arcuate or curved manner over the membrane.

33. The apparatus of claim 29 wherein the at least one membrane defines a meshed membrane.

34. The apparatus of claim 29 further comprising a dilator which is translatable relative to the barrier, wherein distal translation of the dilator engages the aperture and transitions the barrier to a low-profile configuration.

35. The apparatus of claim 29 wherein the aperture has a diameter of 1 to 4 mm.

36. The apparatus of claim 29 wherein the imaging element comprises a CCD, CMOS, or optical fiber imager.

37. The apparatus of claim 29 further comprising an energizable element positionable in proximity to the aperture.

38. A method for controlling fluid flow, comprising:
reconfiguring a barrier projecting distally from a deployment catheter to self-expand from a low-profile configuration to an expanded configuration which defines an open area and where a membrane extends over a distal opening defined by the barrier and partially encloses the open area;
positioning the membrane in proximity or adjacent to a tissue region of interest; and,
infusing a clearing fluid into the open area while visualizing through the open area via an imaging element such that the fluid is purged at least partially through at least one aperture defined along the membrane from the open area to an environment external to the barrier, wherein flow of the fluid from the open area to the environment is inhibited by the aperture.

39. The method of claim 38 wherein visualizing within the imaging element comprises a CCD, CMOS, or optical fiber imager.

40. The method of claim 38 further comprising adjusting a size of the at least one aperture.

41. The method of claim 38 further comprising advancing a dilator into the open area such that the dilator engages the aperture.

42. The method of claim 41 further advancing the dilator relative to the barrier such that the barrier collapses into a low-profile configuration against the dilator.

43. The method of claim 38 further comprising advancing an instrument into the open area to treat tissue underlying the barrier.

44. The method of claim 38 further comprising ablating the tissue while visualizing through the open area.

45. The method of claim 38 wherein ablating the tissue comprises ablating the tissue defined by the at least one aperture.

* * * * *